(12) United States Patent
Finburgh et al.

(10) Patent No.: US 8,777,862 B2
(45) Date of Patent: Jul. 15, 2014

(54) APPARATUS AND METHODS FOR NON-INVASIVELY MEASURING A PATIENT'S ARTERIAL BLOOD PRESSURE

(75) Inventors: Simon E. Finburgh, San Diego, CA (US); Andrew S. Katayama, Cardiff-by-the-Sea, CA (US); Ronald J. Vidischak, Escondido, CA (US); Anthony T. Butler, San Diego, CA (US); Kurt Blessinger, DelMar, CA (US)

(73) Assignee: Tensys Medical, Inc., San Diego, CA (US)

(*) Notice: Subject to any disclaimer, the term of this patent is extended or adjusted under 35 U.S.C. 154(b) by 979 days.

(21) Appl. No.: 12/287,630

(22) Filed: Oct. 9, 2008

(65) Prior Publication Data

US 2009/0131806 A1    May 21, 2009

Related U.S. Application Data

(60) Provisional application No. 60/998,632, filed on Oct. 12, 2007.

(51) Int. Cl.
*A61B 5/02* (2006.01)

(52) U.S. Cl.
USPC ........... 600/485; 600/481; 600/490; 600/494; 600/500; 600/504

(58) Field of Classification Search
USPC ............ 600/481–507; 606/201–202; 128/898
See application file for complete search history.

(56) References Cited

U.S. PATENT DOCUMENTS

| | | | |
|---|---|---|---|
| 6,132,382 A | 10/2000 | Archibald et al. | |
| 6,176,931 B1 | 1/2001 | Restaino et al. | |
| 6,241,679 B1 | 6/2001 | Curran | |
| 6,554,774 B1 | 4/2003 | Miele | |
| 6,695,789 B2 * | 2/2004 | Thede et al. | 600/494 |
| 6,730,038 B2 | 5/2004 | Gallant | |
| 6,974,419 B1 | 12/2005 | Voss | |
| 7,048,691 B2 | 5/2006 | Miele | |
| 7,291,112 B2 | 11/2007 | Martin | |
| 2002/0055680 A1 | 5/2002 | Miele | |
| 2004/0073123 A1 | 4/2004 | Hessel | |
| 2005/0080345 A1 | 4/2005 | Finburgh | |
| 2006/0079792 A1 | 4/2006 | Finburgh | |
| 2006/0184051 A1 | 8/2006 | Hempstead | |
| 2007/0021674 A1 * | 1/2007 | Thede et al. | 600/503 |
| 2008/0021334 A1 * | 1/2008 | Finburgh et al. | 600/490 |

* cited by examiner

*Primary Examiner* — Melanie Y Brown
*Assistant Examiner* — Erik B Crawford
(74) *Attorney, Agent, or Firm* — Gazdzinski & Associates, PC

(57) ABSTRACT

Improved apparatus and methods for non-invasively assessing one or more hemodynamic parameters associated with the circulatory system of a living organism. In one aspect, the invention comprises an apparatus adapted to automatically and accurately place and maintain a sensor (e.g., tonometric pressure sensor) with respect to the anatomy of the subject. The apparatus comprised of a sensor device removably coupled to an actuator which is used to position the sensor during measurements. Methods for positioning the alignment apparatus and sensor, and operating the apparatus, are also disclosed.

20 Claims, 14 Drawing Sheets

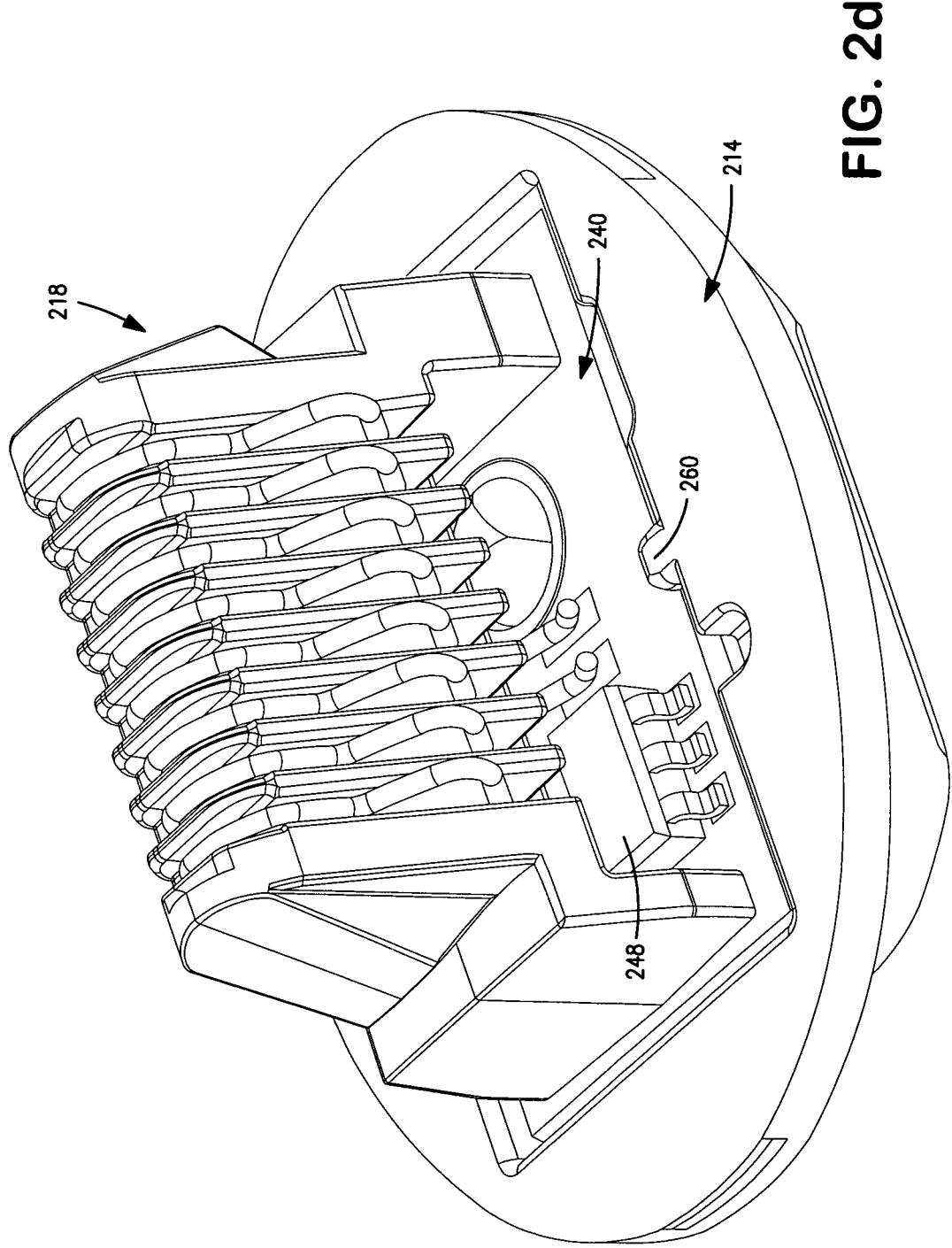

APPARATUS AND METHODS FOR NON-INVASIVELY MEASURING A PATIENT'S ARTERIAL BLOOD PRESSURE

PRIORITY

This application claims priority to U.S. Provisional Patent Application Ser. No. 60/998,632 filed Oct. 12, 2007 of the same title, which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

This invention relates generally to methods and apparatus for monitoring parameters associated with fluid systems, and specifically in one aspect to the non-invasive monitoring of arterial blood pressure in a living subject.

2. Description of Related Art

The accurate measurement of physiological parameters from a living subject has long been sought by medical science. One such area of particular importance is the non-invasive, continuous measurement of blood pressure and/or other hemodynamic parameters. The availability of such measurement techniques would allow the caregiver to continuously monitor a subject's parameters (e.g., blood pressure) accurately and in repeatable fashion without the use of invasive arterial catheters (commonly known as "A-lines") in any number of settings including, for example, surgical operating rooms where continuous, accurate indications of true blood pressure are often essential.

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers generally to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement. Additionally, the methodology for proper initial and follow-on placement is awkward, essentially relying on the caregiver to manually locate the optimal location for sensor placement on the subject each time, and then mark that location (such as by keeping their finger on the spot, or alternatively marking it with a pen or other marking instrument), after which the sensor is placed over the mark. Alternatively, some prior art techniques rely on additional sensing elements and associated apparatus for positioning the sensor. Utilization of additional apparatus results in increased costs and additional steps for implementing the technology.

Prior art tonometry systems are also commonly quite sensitive to the orientation of the pressure transducer on the subject being monitored. Specifically, such systems show degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches similarly suffer from not being able to maintain a constant angular relationship with the artery regardless of lateral position, due in many cases to positioning mechanisms which are not adapted to account for the anatomic features of the subject, such as curvature of the wrist surface.

Another deficiency of prior art non-invasive hemodynamic measurement technology relates to the lack of disposability of components associated with the device. Specifically, it is desirable to make portions of the device which may (i) be contaminated in any fashion through direct or indirect contact with the subject(s) being monitored); (ii) be specifically calibrated or adapted for use on that subject; (iii) lose calibration through normal use, thereby necessitating a more involved recalibration process (as opposed to simply replacing the component with an unused, calibrated counterpart), or (iv) disposable after one or a limited number of uses. This feature is often frustrated in prior art systems based on a lack of easy replacement of certain components (i.e., the components were not made replaceable during the design process), or a prohibitively high cost associated with replacing components that are replaceable. Ideally, certain components associated with a non-invasive hemodynamic assessment device would be readily disposable and replaced at a very low cost to the operator.

Yet another disability of the prior art concerns the ability to conduct multiple hemodynamic measurements on a subject at different times and/or different locations. For example, where blood pressure measurements are required in first and second locations (e.g., the operating room and recovery room of a hospital), prior art methodologies necessitate either (i) the use of an invasive catheter (A-line), (ii) transport of the entire blood pressure monitoring system between the locations, or (iii) disconnection of the subject at the first monitoring location, transport, and then subsequent connection to a second blood pressure monitoring system at the second location.

The disabilities associated with invasive catheters are well understood. These include the need to perforate the subject's skin (with attendant risk of infection), and discomfort to the subject.

Transport of the entire blood pressure monitoring system is largely untenable, due to the bulk of the system and the desire to maintain monitoring equipment indigenous to specific locations.

Disconnection and subsequent reconnection of the subject is also undesirable, since it requires placing a sensor or apparatus on the patient's anatomy a second time, thereby necessitating recalibration, and reducing the level of confidence that the measurements taken at the two different locations are in fact directly comparable to one another. Specifically, since the sensor and supporting apparatus is physically withdrawn at the first location, and then a new sensor subsequently placed again on the subject's tissue at the second location, the likelihood of having different coupling between the sensor and the underlying blood vessel at the two locations is significant. Hence, identical intra-vascular pressure values may be reflected as two different values at the different locations due to changes in coupling, calibration, sensor parameters, and related factors, thereby reducing the repeatability and confidence level associated the two readings.

Additionally, in the prior art, the sensor is often electrically connected to an actuator other host device via an external electrical connection via a cable or "pigtail". Such connection apparatus adds additional costs and complexity to the system.

Based on the foregoing, there is a need for an improved apparatus and methodology for accurately, continuously, and non-invasively measuring parameters (such as for example those associated with the hemodynamic system) associated with a living subject. Such improved apparatus and methodology would ideally allow for prompt and accurate initial placement of the sensor(s) (e.g., a tonometric pressure sensor, ultrasonic sensor, etc.) without requiring additional alignment apparatus or elements, while also providing robustness and repeatability of placement under varying patient physiology and environmental conditions. Such apparatus would also incorporate low-cost and disposable components.

Such apparatus and methods would furthermore be substantially self-aligning and calibrating (i.e., automatically place itself and "zero" itself) with respect to a patient. Ease of use would also be considered.

SUMMARY OF THE INVENTION

The present invention satisfies the aforementioned needs by an improved apparatus and methods for non-invasively and continuously assessing hemodynamic properties, including arterial blood pressure, within a living subject.

In a first aspect of the invention, an apparatus adapted to measure at least one hemodynamic parameter of a living subject is disclosed. The apparatus is comprised in one embodiment of a sensor assembly adapted to substantially conform to the anatomy of the subject. This is accomplished via a frame comprising a conforming element and a hemodynamic pressure sensor element coupled to the frame. In one variant, the pressure sensor element is coupled to the frame by a flexible support structure. In another variant, the sensor element further comprises an electrical interface adapted for direct simultaneous mating with a corresponding connector of an actuator when the sensor element is mechanically mated to the actuator.

In another embodiment, the apparatus comprises a substantially conformal frame; and a sensor element, the sensor element coupled to the frame by an at least partly flexible support structure. The sensor element further comprises an electrical interface, and the sensor element is configured so as to form an electrical connection with a corresponding electrical interface of a host device simultaneously during mating of the sensor element to the host device.

In one variant, the sensor element comprises a blood pressure sensor, and further comprises: a biasing element; a pressure transducer; a plurality of electrical conductors disposed on at least one printed circuit board and adapted to electrically interface with the host device; and a housing element adapted to encase at least a portion of the sensor element.

In another variant, the housing element comprises a substantially pyramid-shaped portion, at least a portion of the electrical conductors being disposed thereon.

In a further variant, the host device comprises an actuator, and the at least partly flexible support structure comprises a plurality of at least partly arcuate linkages.

In yet another variant, the mating of the sensor element to the host device is facilitated via one or more retention features on the frame and the sensor element.

In another variant, the frame has a substantially smaller surface area on a radial side than on an ulnar side when disposed on the subject.

In still another variant, the frame further comprises a substantially compliant foam backing having at least one adhesive surface adapted to adhere to tissue of the subject.

In another variant, the assembly comprises apparatus adapted to facilitate alignment of the sensor element above an artery of the subject without the use of an external alignment apparatus.

In another embodiment of the apparatus, the apparatus comprises: a support element, comprising a conforming element adapted to substantially conform to the anatomy of the subject; and a sensing apparatus flexibly coupled to the support element, the sensing apparatus comprising a combined electrical and mechanical interface, the sensing apparatus adapted to be at least initially aligned into position over an artery of the living subject without utilizing any additional alignment apparatus. The combined electrical and mechanical interface comprises one or more features adapted to mate the sensing apparatus to a host device.

In one variant, the combined interface of the sensing apparatus comprise at least a plurality of electrical conductors disposed on at least one printed circuit board.

In another variant, the support element further comprises an alignment element adapted to assist in the alignment of the sensing apparatus over the artery, and the alignment element comprises at least one arrow, the arrow being adapted to align with at least a point associated with an artery of the subject.

In yet another variant, the sensing apparatus is flexibly coupled to the support element via (i) a substantially resilient suspension loop encircling at least a portion of the sensing apparatus, and (ii) one or more associated suspension arms joining the loop to the support element.

In a further variant, the apparatus further comprises a second support element adapted to stabilize the sensing apparatus.

In still another embodiment of the apparatus, the apparatus comprises: a sensor assembly comprising: a biasing element; a pressure sensor; and a connector adapted to electrically connect to a recessed portion of a sensor assembly actuator; and a substantially flexible frame element adapted to: flexibly support the sensor assembly, the support further enabling the sensor assembly to be moved by an actuator substantially within the frame element; at least partly conform to the anatomy of the subject proximate the blood vessel; and provide an optical alignment feature to aid an operator in placing the apparatus on the subject.

In one variant, the sensor assembly further comprises a multi-layered housing element, the housing element adapted to encase at least a portion of the connector, and the electrical connection between the connector and the actuator is accomplished via one or more friction fit features disposed on the housing element or the frame.

In another variant, the connector comprises a plurality of electrical conductors disposed on a printed circuit board and adapted to electrically connect with electrical components of the recessed portion of the actuator.

In yet another variant, the sensor assembly further comprises a substantially compliant contact material adapted to interface between an active surface of the transducer and tissue of the subject.

In still a further variant, the sensor assembly is physically connected to the frame element by at least one substantially flexible serpentine arm.

In a second aspect of the invention, hemodynamic sensor is disclosed. In one embodiment, the sensor comprises a substantially oval or elliptically shaped sensor having a pressure sensor, one or more electronic data storage devices, and an electrical interface to a parent device (e.g., actuator). The sensing face of the sensor is substantially covered with a pliable material (e.g., silicone-based compound) that couples the sensor active area to the subject's skin surface.

In another embodiment, the sensor apparatus comprises: a biasing element; a pressure sensor; a connector, the connector comprising: one or more electronic data storage devices; and a sensor electrical interface adapted to electrically connect to a corresponding electrical interface that is disposed at least partly within a recessed portion of a host device; and a housing element adapted to enclose at least a portion of the electrical interface. The sensor electrical interface is adapted to mate with the corresponding interface simultaneously during the mechanical mating of the sensor apparatus to the host device.

In one variant, the sensor electrical interface is comprised of a plurality of electrical conductors disposed on at least one printed circuit board and formed into a substantially pyramidal shape.

In another variant, the mechanical mating comprises frictional coupling of one or more features disposed on the housing element with one or more corresponding features disposed on the host device.

In a further variant, the sensor apparatus is substantially elliptically shaped.

In still another variant, a sensing face of the sensor is substantially covered with a pliable material adapted to couple the sensing face the surface of the skin of a living subject.

In a third aspect of the invention, apparatus for non-invasively measuring the pressure in a subject's blood vessel is disclosed. In one variant, the apparatus comprises: a sensor, and support element, and an actuator apparatus. The actuator apparatus couples to the support element and the sensor, the latter being movably coupled to the actuator. In another variant, a second support element is used to further stabilize the actuator. This second element may comprise for example an arm brace or similar structure.

In a fourth aspect of the invention, a method of operating an apparatus is disclosed. In one embodiment, the apparatus comprises a hemodynamic assessment apparatus, and the method comprises: disposing a sensor proximate to a blood vessel; coupling an actuator to the sensor; calibrating the sensor; and measuring the hemodynamic parameter. In one variant, the sensor is disposed onto the subject's anatomy using a disposable support element which is movably coupled to the sensor. The actuator can be electrically and mechanically coupled simply by "snapping" the actuator into place on the support element.

In another embodiment, the method comprises: disposing a sensor proximate to a blood vessel of the subject, the sensor being substantially supported by a flexible coupling to a support element; coupling an actuator to the sensor; calibrating the sensor; and measuring the one or more hemodynamic parameters. The coupling comprises electrically and mechanically coupling the sensor to the actuator in a single user action. In one variant, the act of disposing comprises disposing the support element such that the sensor is generally proximate the blood vessel.

In another variant, the act of calibrating comprises using a positioning algorithm to adjust the position of the sensor with respect to the blood vessel so that the measuring is substantially optimized.

In a fifth aspect of the invention, a method of measuring one or more physiologic parameters of a living subject is disclosed. In one embodiment, the method comprises: disposing at least one sensor element on the subject; mating the sensor element to a host device; using the host device to automatically position the sensor element at a prescribed monitoring location, and calibrate the sensor element; and measuring the one or more parameters of the subject using the sensor element.

In one variant, the act of positioning the sensor element further comprises automatically zeroing the sensor with respect to the placement of the sensor element on the subject. The automatic zeroing comprises for example at least one of: checking for a quiescent state comprising a substantially steady sensor electrical output; and retracting the sensor away from tissue of the living subject, and performing one or more sample applanation functions.

In another variant, the mating of the host device with the sensor element comprises simultaneously forming both electrical and mechanical connections.

In still another variant, the method further comprises: decoupling the host device from the sensor element; re-mating the host device and the sensor element after a period of time; and obtaining second measurements of the one or more hemodynamic parameters of the subject without having to recalibrate the sensor element.

In another variant, the method further comprises determining whether a sensor element is coupled to the host device by at least: attempting to couple the sensor to the host device; and evaluating whether proper mechanical and electrical coupling has been achieved by evaluating the presence of an electrical attribute associated with the sensor element. The attribute comprises for example at least one of: determining whether electrical continuity between the sensor element and host device exists; or attempting to access a storage device on the sensor element using circuitry in the host device.

In a sixth aspect of the invention, a method of providing treatment is disclosed.

In a seventh aspect of the invention a method, of determining whether a sensor element is coupled to an actuator element is disclosed. In one embodiment, the method comprises: attempting to couple the sensor to the actuator; and evaluating whether proper mechanical and electrical coupling has been achieved by evaluating the presence of an electrical attribute associated with the sensor. In one variant, the attribute comprises determining whether electrical continuity between the sensor and actuator exists. In another variant, the attribute comprises attempting to access a storage device on the sensor using circuitry in the actuator.

In an eighth aspect of the invention, a method of positioning at least one sensor with respect to the anatomy of a living subject. In one embodiment, the method comprises: providing the at least one sensor; determining a general location for disposal of the at least one sensor; disposing the at least one sensor at the general location using only an alignment apparatus that is coupled to the at least one sensor; coupling the at least one sensor to an actuator; and adjusting the general location of the at least one sensor using the actuator.

In one variant, the adjusting comprises implementing a position location algorithm. For example, the position location algorithm comprises at least one of: checking for a quiescent state having a substantially steady sensor output; or retracting the sensor and performing one or more applanation functions.

In another variant, the act of determining a general location for disposal of the at least one sensor comprises manually locating an artery of the subject.

In a ninth aspect of the invention, a method and apparatus for automatic zeroing of the hemodynamic assessment apparatus are disclosed.

These and other features of the invention will become apparent from the following description of the invention, taken in conjunction with the accompanying drawings.

BRIEF DESCRIPTION OF THE DRAWINGS

FIG. 2b is an illustration of the sensor connector of the exemplary embodiment of the sensor connector assembly of FIG. 2a.

FIG. 2d is an illustration of the sensor connector, pressure sensor and EEPROM of the exemplary embodiment of the sensor connector assembly mounted on a printed circuit board and placed in the connector housing.

FIG. 3a is a cross-sectional view of the mated actuator and sensor assembly of FIG. 3a.

FIG. 3b is a break-away view of the mated actuator and sensor assembly of FIG. 3a.

DETAILED DESCRIPTION OF THE INVENTION

Figure 1:
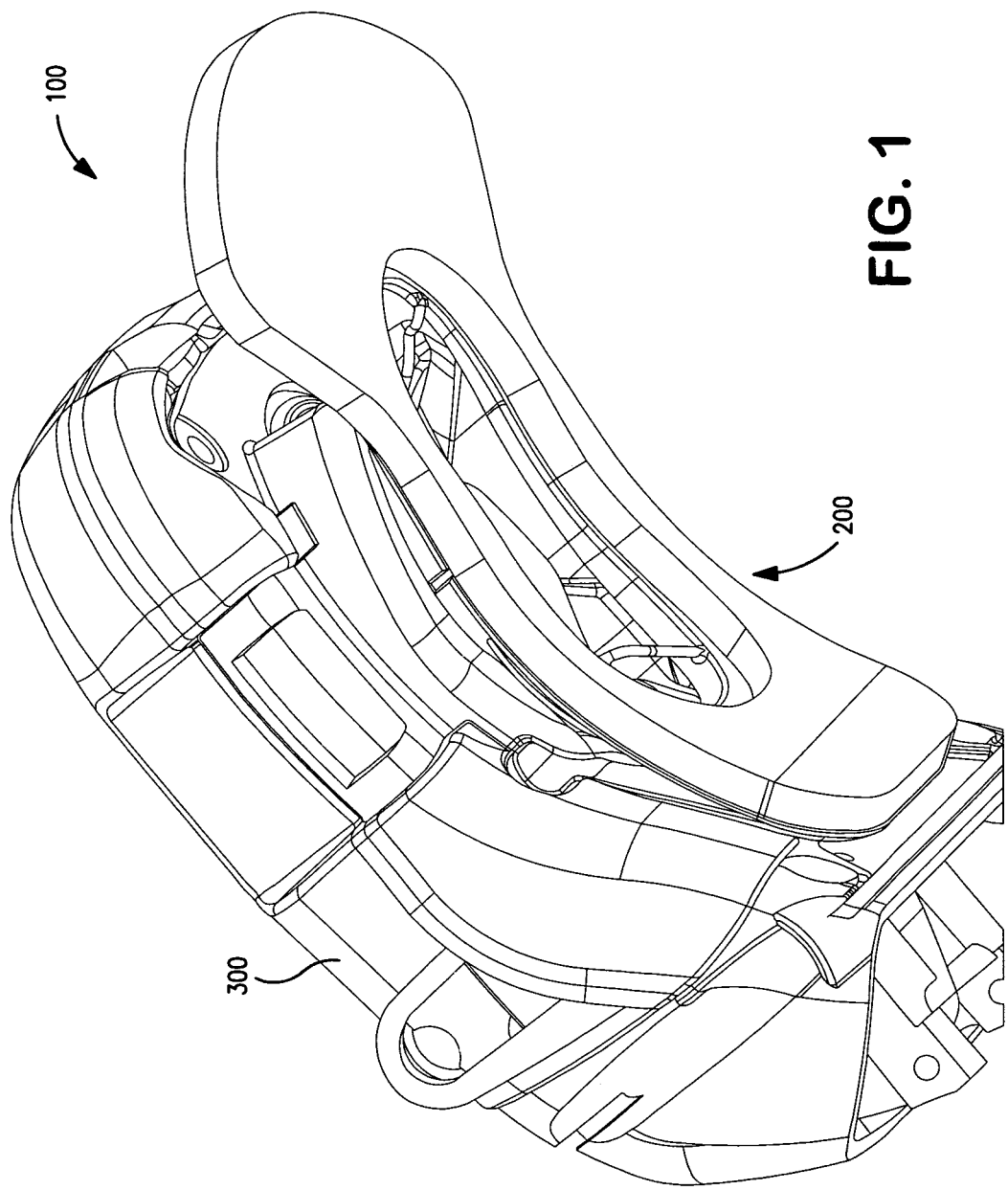
FIG. 1 is a bottom perspective view of one exemplary embodiment of the hemodynamic assessment apparatus of the present invention, shown with sensor assembly coupled to the top portion of the actuator assembly.

Reference is now made to the drawings wherein like numerals refer to like parts throughout.

It is noted that while the invention is described herein primarily in terms of a method and apparatus for assessment of hemodynamic parameters of the circulatory system via the radial artery (i.e., wrist or forearm) of a human subject, the invention may also be readily embodied or adapted to monitor such parameters at other blood vessels and locations on the human body, as well as monitoring these parameters on other warm-blooded species. All such adaptations and alternate embodiments are readily implemented by those of ordinary skill in the relevant arts, and are considered to fall within the scope of the claims appended hereto.

As used herein, the term "hemodynamic parameter" is meant to include parameters associated with the circulatory system of the subject, including for example pressure (e.g., diastolic, systolic, pulse, or mean), blood flow kinetic energy, velocity, density, time-frequency distribution, the presence of stenoses, $SpO_2$, pulse period, as well as any artifacts relating to the pressure waveform of the subject.

Additionally, it is noted that the terms "tonometric," "tonometer," and "tonometry" as used herein are intended to broadly refer to non-invasive surface measurement of one or more hemodynamic parameters such as pressure, such as by placing a sensor in communication with the surface of the skin, although contact with the skin need not be direct (e.g., such as through a coupling medium or other interface).

The terms "applanate" and "applanation" as used herein refer to the compression (relative to a state of non-compression) of tissue, blood vessel(s), and other structures such as tendon or muscle of the subject's physiology. Similarly, an applanation "sweep" refers to one or more periods of time during which the applanation level is varied (either increasingly, decreasingly, or any combination thereof). Although generally used in the context of linear (constant velocity) position variations, the term "applanation" as used herein may conceivably take on any variety of other forms, including without limitation (i) a continuous non-linear (e.g., logarithmic) increasing or decreasing compression over time; (ii) a non-continuous or piece-wise continuous linear or non-linear compression; (iii) alternating compression and relaxation; (iv) sinusoidal or triangular waves functions; (v) random motion (such as a "random walk"; or (vi) a deterministic profile. All such forms are considered to be encompassed by the term.

As used herein, the term "integrated circuit (IC)" refers to any type of device having any level of integration (including without limitation ULSI, VLSI, and LSI) and irrespective of process or base materials (including, without limitation Si, SiGe, CMOS and GaAs). ICs may include, for example, memory devices (e.g., DRAM, SRAM, DDRAM, EEPROM/Flash, ROM), digital processors, SoC devices, FPGAs, ASICs, ADCs, DACs, transceivers, memory controllers, and other devices, as well as any combinations thereof.

As used herein, the term "memory" includes any type of integrated circuit or other storage device adapted for storing digital data including, without limitation, ROM. PROM, EEPROM, DRAM, SDRAM, DDR/2 SDRAM, EDO/FPMS, RLDRAM, SRAM, "flash" memory (e.g., NAND/NOR), and PSRAM.

Overview

In one fundamental aspect, the present invention comprises apparatus and associated methods for accurately and repeatably (if desired) disposing one or more sensors with respect to the anatomy of a subject to facilitate subsequent hemodynamic parameter measurements using the sensor(s). For example, as will be described in greater detail below, the present invention is useful for accurately placing a pressure sensor assembly for continuously and non-invasively measuring the blood pressure from the radial artery of a human being. However, literally any kind of sensor (ultrasound, optical, etc.) can be used alone or in combination consistent with the invention, including for example the devices and associated techniques described in co-pending U.S. patent application Ser. No. 10/961,460 filed Oct. 7, 2004 and entitled "Compact Apparatus and Methods For Non-Invasively Measuring Hemodynamic Parameters", U.S. patent application Ser. No. 09/815,982 filed Mar. 22, 2001 and entitled "Method and Apparatus for the Noninvasive Assessment of Hemodynamic Parameters Including Blood Vessel Location", and U.S. patent application Ser. No. 09/815,080 filed Mar. 22, 2001 entitled "Method and Apparatus for Assessing Hemodynamic Parameters within the Circulatory System of a Living Subject", now U.S. Pat. No. 7,048,691, each of which are assigned to the assignee hereof and incorporated herein by reference in their entirety.

In one exemplary embodiment, the aforementioned pressure sensor is coupled to an actuator mechanism carried by a brace or "bracelet" assembly worn by the subject in the area of the radial artery. The actuator mechanism, when coupled to the sensor, controls the sensor lateral (and proximal, if desired) position as well as the level of applanation of the underlying tissue according to any number of control schemes, including for example that set forth in Assignee's co-pending U.S. patent application Ser. No. 10/211,115 filed Aug. 1, 2002, entitled "Method and Apparatus for Control of Non-Invasive Parameter Measurements", now U.S. Pat. No. 6,974,419, and in co-pending application Ser. No. 10/072,508 filed Feb. 5, 2002, entitled "Method and Apparatus for Non-Invasively Measuring Hemodynamic Parameters Using Parametrics," now U.S. Pat. No. 6,730,038, both of which are incorporated herein by reference in their entirety. However, the present invention is also compatible with systems having separate sensor(s) and applanation mechanisms, as well as combinations of the foregoing features and sensors. The actuator is advantageously "displacement" driven, and accordingly does not rely on measurements of applied force, but rather merely displacement. This approach greatly simplifies the construction and operation of the actuator (and parent control system) by obviating force sensors and signal processing relating thereto, and further makes the actuator and system more robust.

The apparatus of the present invention also advantageously maintains a highly rigid coupling between the sensor assembly and the bracelet element (actuator) used to receive the subject's anatomy, thereby further enhancing the accuracy of the system through elimination of nearly all compliance within the apparatus.

In another aspect, the present invention is superior to the prior art in that it incorporates automatic zeroing of the sensor. The automatic zeroing capability permits the sensor connector assembly to be positioned without the use of additional elements thereby supporting efficient placement of the sensor.

Another significant feature of the present invention is that it incorporates electrical circuitry directly on the sensor so as to facilitate simplified assembly, operation and calibration of the assembly.

Other significant features of the present invention include (i) ease of use under a variety of different operational environments; (ii) repeatability of measurements; and (iii) disposability of certain components. These features are achieved through the use of novel structures and techniques for placing the sensor(s) and operating the device, as well as significant modularity in design and consideration of the constraints relating to the typical (and atypical) clinical environment.

In one aspect, the present invention overcomes the disabilities associated with the prior art by providing a sensor assembly which is detachable from the parent apparatus and remains positioned on the subject during transport, thereby facilitating highly repeatable measurements using the same sensor at different physical locations within the care facility (e.g., hospital), as described in Assignee's co-pending U.S. patent application Ser. No. 11/336,222 filed Jan. 20, 2006 entitled "Apparatus and methods for non-invasively measuring hemodynamic parameters" which Assignee hereby incorporates by reference in its entirety. The abovementioned features and other features are now described in detail.

Apparatus for Hemodynamic Assessment

Referring now to FIG. 1, an exemplary embodiment of the hemodynamic assessment apparatus 100 of the invention is described. This embodiment generally comprises an actuator assembly 300 mated with a sensor assembly 200. The actuator 300 is optionally in the form of a wrist bracelet as shown, and controls the movement of the sensor/applanation element 210 of the sensor assembly 200. The sensor assembly 200 comprises a flexible frame 204 with a foam backing 206. The sensor assembly 200 is further described in detail with regard to FIGS. 2-2g below.

In the illustrated embodiment, this structure is preferably made disposable through use of inexpensive materials (e.g., low-cost plastic moldings) and design features facilitating such disposability; however in certain applications (such as where the apparatus is intended for reuse), more durable materials may be chosen.

Noticeably distinct from the prior art, the aforementioned embodiment of the hemodynamic assessment apparatus does not comprise an alignment apparatus (e.g., paddle) as in prior embodiments. Rather, the exemplary embodiment of the present invention is adapted to utilize automatic zeroing, a technique by which the sensor element is aligned without the use of extraneous apparatus. Thus, the sensor element will be automatically positioned in the most appropriate location relative to the subject's anatomy.

In one variant of the invention, the frame 204 incorporates arrows that are used to align with a line drawn on the patient's arm (e.g., by the caregiver after manually locating the optimal location on the subject's anatomy which represents the artery location). The clinician palpates and marks the artery with a pen on the skin, drawing a line where the artery lies. Then he/she lines the two arrows on the top of the frame with the line drawn on the skin.

Figure 2:
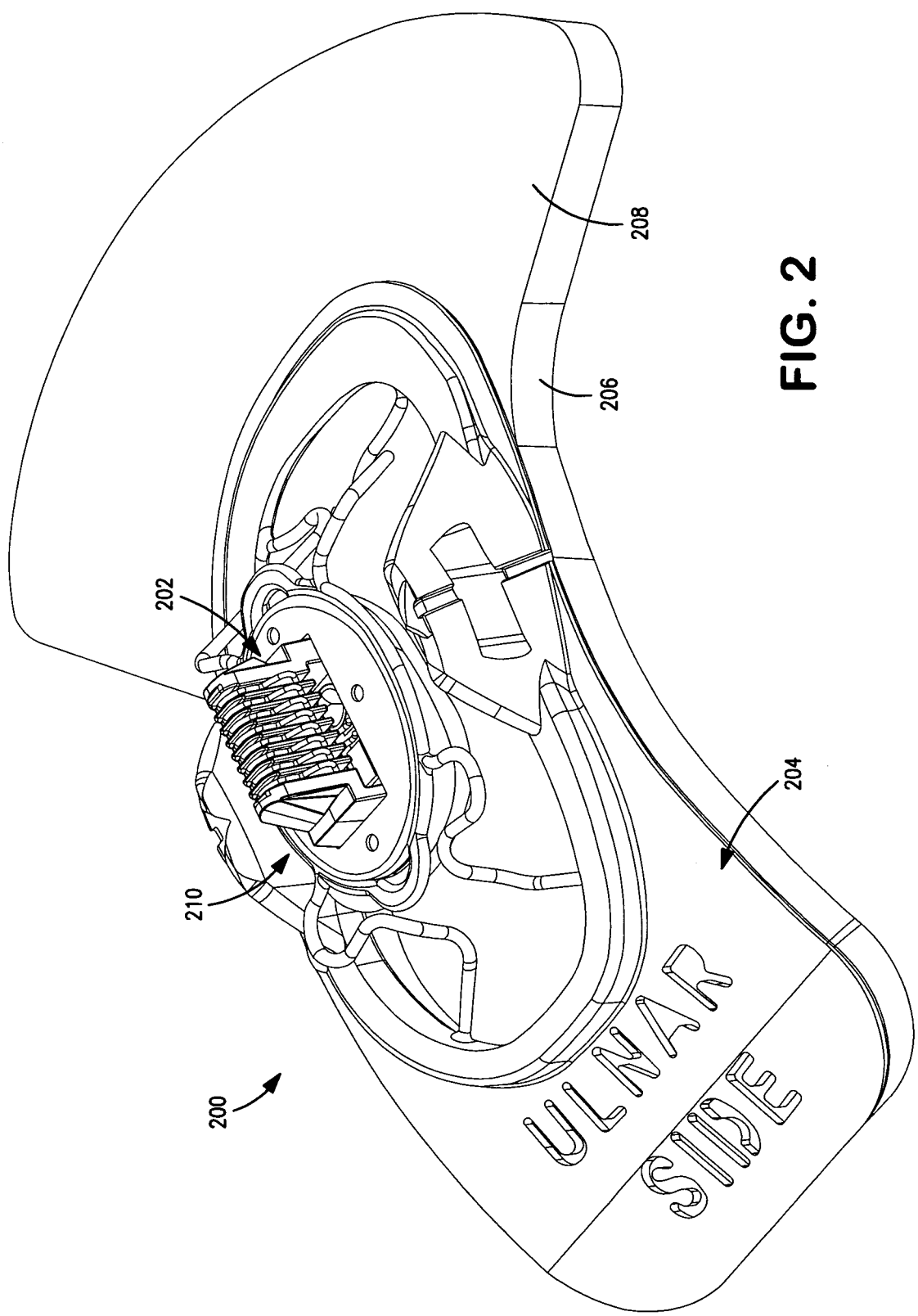
FIG. 2 is a perspective view of one exemplary embodiment of the sensor assembly used with the apparatus of FIG. 1.

FIG. 2 depicts an exemplary embodiment of a sensor assembly 200. As illustrated, the sensor assembly 200 generally comprises a sensor connector assembly 202 (described in more detail in FIG. 2a-2e below) mounted on a sensor element 210, the element 210 being movably coupled to a flexible frame element 204 (described in further detail in FIG. 2f below), the latter which comprises a foam backing 206 (described in detail in FIG. 2g below).

In one embodiment, the sensor assembly 200 further comprises a label or other covering 208 which (i) covers the end of the foam which would otherwise be bare adhesive, and (ii) shows inter alia a user the correct placement of the device on the arm. Since the frame ends at the edge of the label, the foam is much more flexible, which allows it to conform better to the wrist. The label of the illustrated allows us to use one piece of foam that has adhesive on the top surface, to attach it to the frame, although it will be appreciated that other approaches may be used with equal success.

Figure 2A:
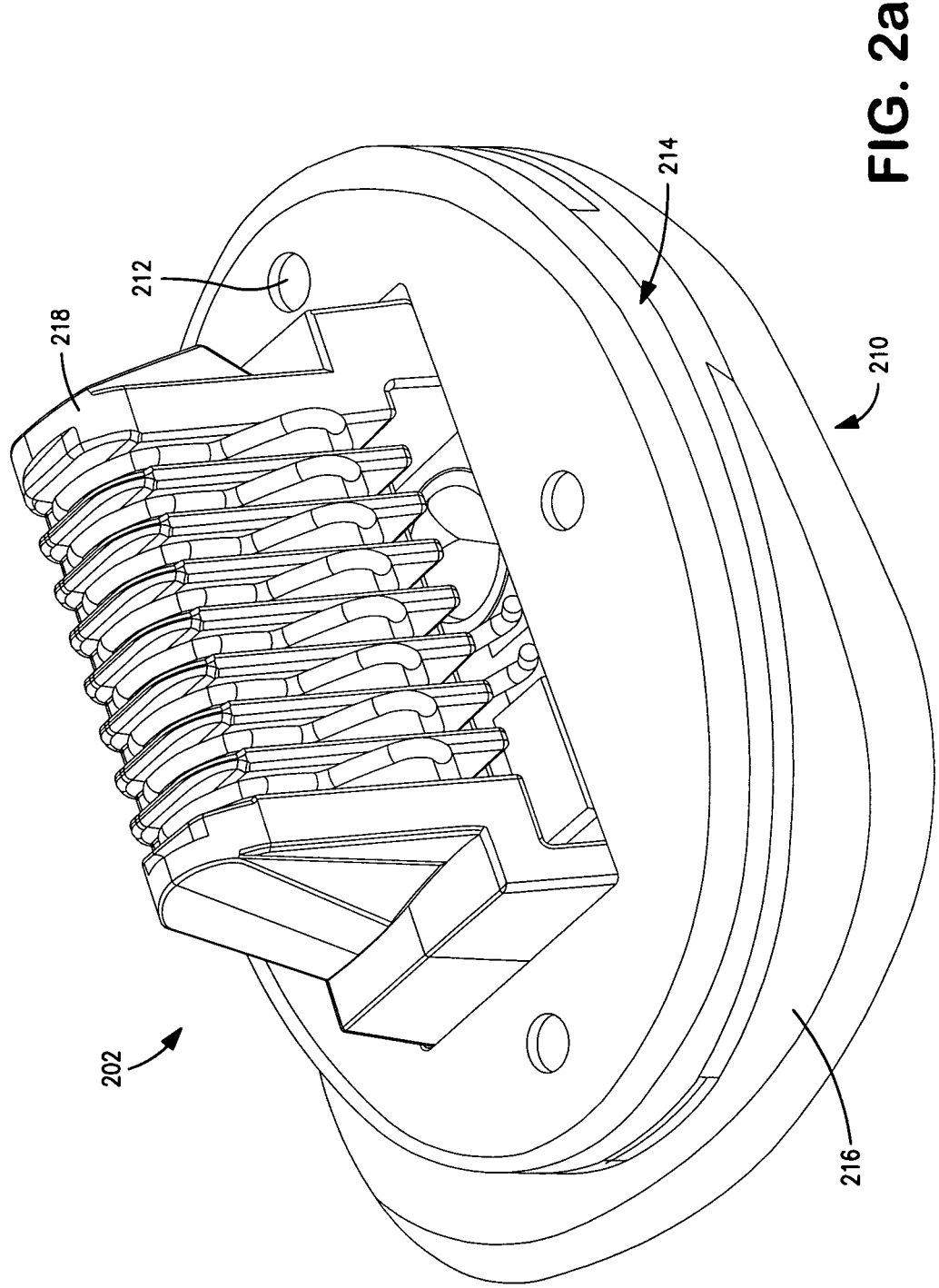
FIG. 2a is an illustration of one exemplary embodiment of the fully encapsulated sensor connector assembly.

FIG. 2a illustrates the sensor connector assembly 202 which is comprised of a sensor connector 218 disposed on the sensor/applanation element 210. The sensor connector assembly 202 is further comprised of an electrically erasable programmable read-only memory (EEPROM) IC (element 248 on FIG. 2c), one or more pressure sensor elements (e.g., a transducer, strain beam device, piezoelectric or piezoresistive device, etc.), and a multi-layered housing element 214. These components of the sensor connector assembly 202 are illustrated and described in more detail in FIGS. 2b-2e and the accompanying discussion below.

The sensor/applanation element 210 is used to compress the tissue surrounding the blood vessel of interest under the force of the actuator 300, and to thereby apply force to the blood vessel wall so as to overcome the wall or hoop stress thereof. The applanation element 210 has a specially designed configuration adapted to mitigate the effects of transfer loss in a simple, repeatable, and reliable way such that it can be either (i) ignored or (ii) compensated for as part of the tonometric measurement.

Figure 2B:
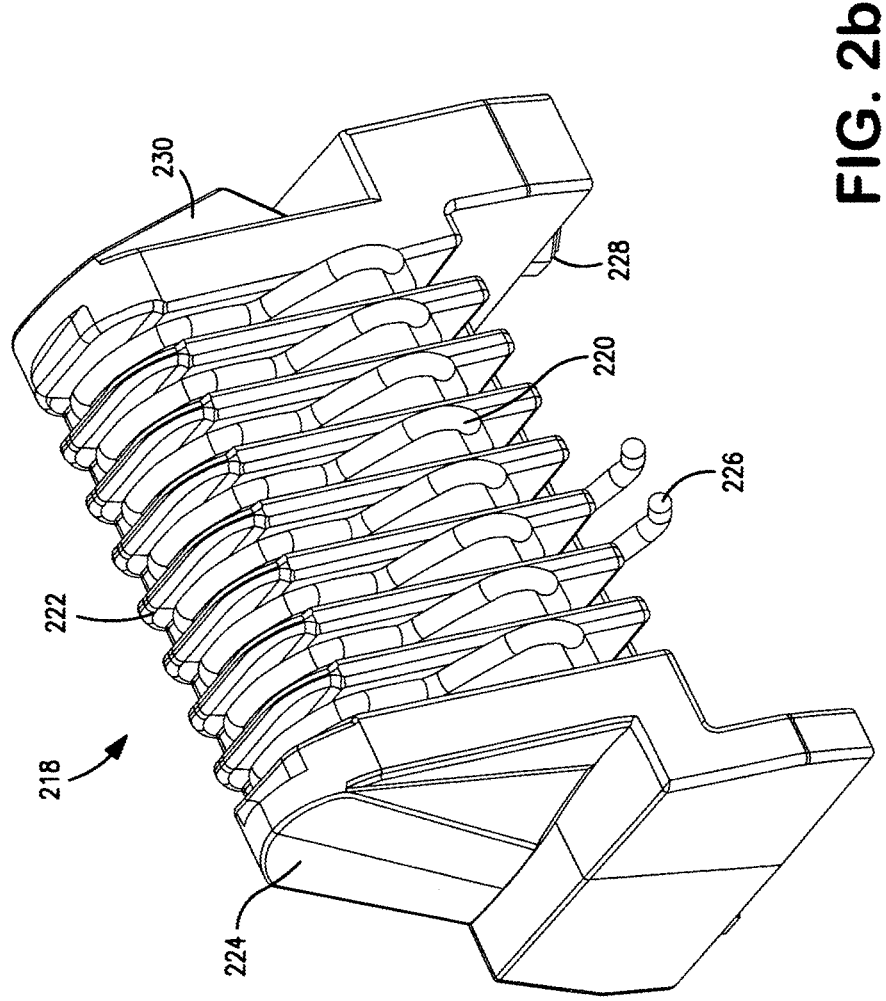

The sensor connector assembly 202 further comprises a sensor connector 218, which may be viewed in more detail in FIG. 2b.

FIG. 2b depicts the sensor connector 218. The sensor connector is comprised of a plurality of conductors (e.g. wires 220 or alternatively flat strips, conductive traces, etc.). The wires follow along the periphery of one side of a generally pyramidal or tapered spool or block 224, although other profiles and shapes (e.g., conic, trapezoidal, hemispherical, hexagonal, etc.) are contemplated. The use of a shape helps to guide the connector into the receptacle without getting stuck or misaligned. The wires 220 are maintained electrically separate from each other by a series of ridges 222 along the inner portion of the pyramidal spool 224. The wires 220 are adapted such that when the sensor connector assembly 202 is mated with the connector recess 308 the actuator 300, the wires 220 are positioned to electrically communicate with the electrical contacts 312 of the recess 308. The exemplary embodiment of the sensor connector 218 as illustrated in FIG. 2b further depicts a plurality of wire terminals 226. It is appreciated that although eight wire terminals 226 are illustrated in the exemplary embodiment, any number of such terminals may be utilized consistent with the present invention. The plurality of exposed wires 220 is made large so as to provide maximum opportunity for making a good connection with the corresponding electrical connector in the actuator, described below. In the illustrated embodiment, two of the eight wires egress from one side of the assembly, and six from the others, so as to provide mechanical stability during assembly.

The overall tapered 230 pyramidal shape of the top portion of the sensor connector 218 is merely exemplary in that it promotes a frictional coupling between the sensor assembly 200 and the associated actuator receptacle 304. Thus, the associated actuator receptacle 304 (see FIG. 3 and associated discussion below) is effectively the inverse of the top portion of the sensor connector 218; i.e., it is adapted to generally match at least most of the contours of the sensor connector 218 and the frame lip 282 (discussed below). Indentions 212 are provided in the top surface of the bottom portion of the sensor element to allow mating to the top portion thereof. The top portion of the sensor connector 218 can be considered the "male" element, and the associated actuator receptacle 304 the "female" element. The substantially square shape of the base of the sensor connector 218 advantageously controls rotation of the sensor connector 218 with respect to the actuator receptacle 304 under torsional loads. This coupling of the two elements 218, 304 allows for a highly rigid and non-compliant joint between the actuator 300 and sensor assembly 200 in the applanation (normal) dimension, thereby effectively eliminating errors in resulting hemodynamic measurements which could arise from such compliance. A discussion of the contribution of the frame lip 282 to this coupling is discussed below.

Figure 2C:
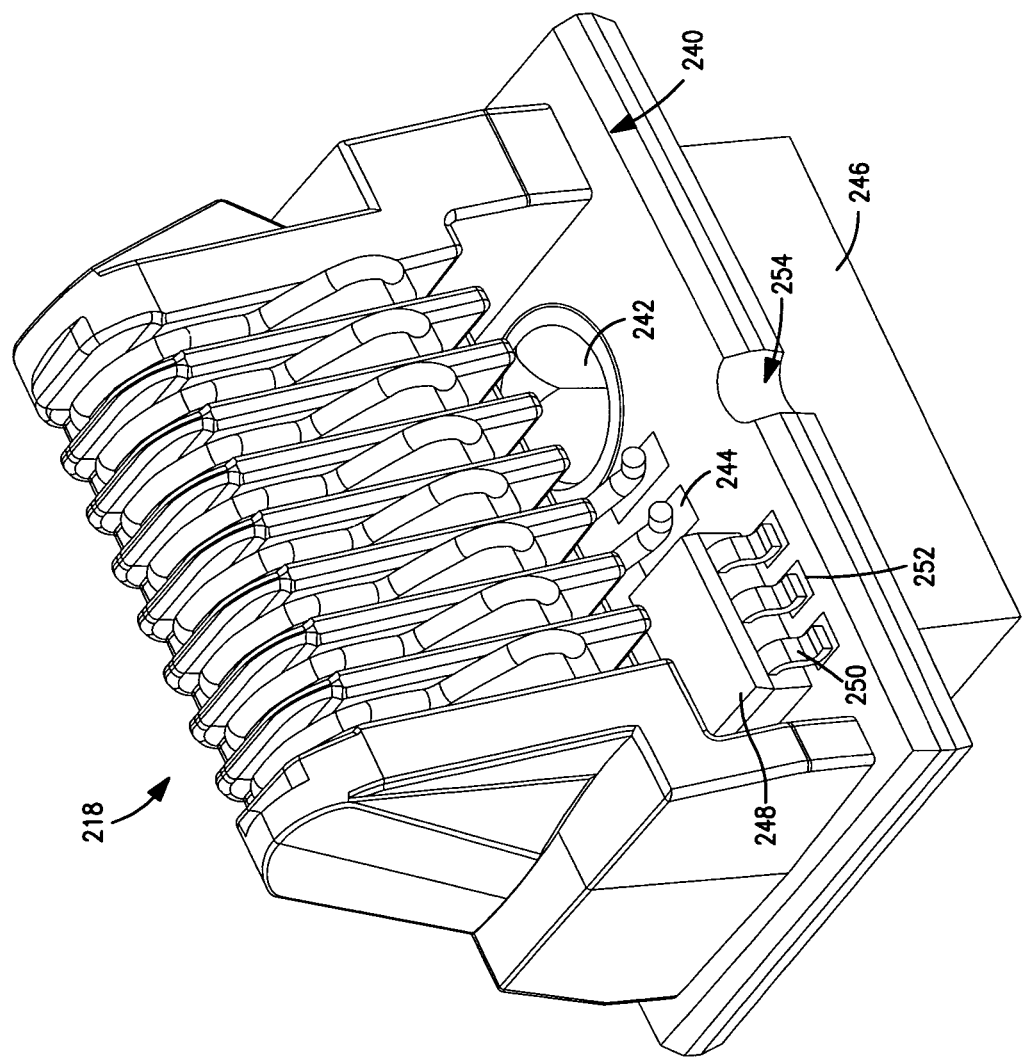
FIG. 2c is an illustration of the sensor connector of the exemplary embodiment of the sensor connector assembly mounted on a printed circuit board with a pressure sensor and a storage device (e.g., EEPROM).

As illustrated in FIG. 2c, the sensor connector assembly 202 further comprises a printed circuit board 240 on which the connector 218 is disposed. The tabs 228 of the sensor connector 218 facilitate mounting the sensor connector 218 on the printed circuit board 240 as they are received in tab recesses (not shown) on the circuit board 240.

The sensor connector wire terminals 226 are situated such that when the sensor connector 218 is mounted on the printed circuit board 240, the wire terminals 226 align with the sensor connector terminal electrical contacts 244 on the printed circuit board 240. It is through this contact that information from the sensor (not shown) is transmitted, although other approaches may be used.

Also as depicted in FIG. 2c, the sensor connector assembly 202 comprises the sensing elements (not shown) accommodated within a lower sensor housing 246 below the sensor connector 218. A retention feature such as, for example, cantilever snap, is used to secure the lower housing element 246 to the other layers of the sensor connector assembly 202. In another embodiment, the sensor has four leads that protrude, and are formed into "legs" that are soldered to the other side of the board. The part is also adhered to the board to ensure it is rigidly held.

The circular feature shown is the vent port protruding from the pressure sensor (246). This vent is a cylinder that sticks through the board and thereby allows for the pressure die in the sensor to be a gage device. It has effectively a vent on each side of the pressure diaphragm, with one side communicating with the silicone rubber gel which touches the skin and the other side of the diaphragm communicating with the air in the environment in which it is being us The sensor elements (not shown) are situated within the lower sensor housing 246 such that the sensor is positioned to contact the skin of a subject. The bias element 216 then forms a substantially elliptical profile "pocket" adapted to house the sensor elements.

Also in FIG. 2c, an electrically erasable programmable read-only memory (EEPROM) IC 248 or other memory device is disposed on the printed circuit board 240. The EEPROM chip terminals 250 are situated such that when the EEPROM chip 248 is disposed on the printed circuit board 240, the terminals 250 are placed in contact with EEPROM terminal electrical contacts 252 on the circuit board 240.

The circular feature 242 shown is a vent port protruding from the pressure sensor 246. This vent is a cylinder that protrudes through the board and thereby allows for the pressure die in the sensor to be a gauge device. It comprises a vent on each side of the pressure diaphragm, with one side communicating with the silicone rubber gel which touches the skin of the subject, and the other side of the diaphragm communicating with the air in the environment in which it is being used. This allows for the device to not read the atmospheric pressure differences at different altitudes.

Given the components described above, the sensor connector assembly 202 in this embodiment is adapted to contain the necessary circuitry and sensor electronics such that the assembly 202, when mated with the actuator 300 will be able to transmit electrical signals from the sensor element(s) (e.g., pressure transducer, not shown) to the actuator 300 without the use of other apparatus. In this way, the assembly can detect and monitor pressure immediately upon electrical connection of the sensor assembly 200 to the actuator 300, and the need to form any other electrical or mechanical connections is obviated. Therefore, the above-described embodiment determines and constantly monitors hemodynamic pressure efficiently and with increased ease of operation.

FIG. 2d illustrates the disposition of the exemplary multi-layered housing element 214 around the printed circuit board 240 containing the EEPROM chip 248 and sensor connector 218. The multi-layered housing element 214, inter alia, helps maintain and encase the printed circuit board 240 and its components. Therefore, the face of the housing element 214 contains an indentation that is substantially formed to suit the printed circuit board 240. Further, the face of the housing element 214 contains a protrusion 260 which aligns with the printed circuit board indention 254 (FIG. 2c). It is of note that each layer of the multi-layered housing element 214 includes various protrusions and complimentary indentions so that the layers may fit together in a unique manner, and may be held together without adhesives or other such mechanisms if desired. Alternatively, the various features can be obviated in favor of such an adhesive or other mechanism. It is appreciated that other mechanisms for hold the housing elements together may be utilized consistent with the present invention. Further, a single layered housing element may also be substituted in place of the multi-layered configuration described herein. In one variant, the assembly is made as a "pallet" of boards that are snapped apart. The connectors and EEPROMs are soldered to one side of this array or matrix of boards, then the sensor is glued and then soldered to the other side of each board. Once separated, they form the assembly shown is FIG. 2c. The housings comprise a housing and a cap to hold the board in the housing. The exemplary cap is made out of ABS plastic and is placed over the connector and then solvent-bonded to the housing, effectively trapping the connector, the board and the sensor in place. Alternative configurations considered included ultrasonically welding the cap to the housing, or snapping the cap to the housing features to allow this.

Figure 2E:
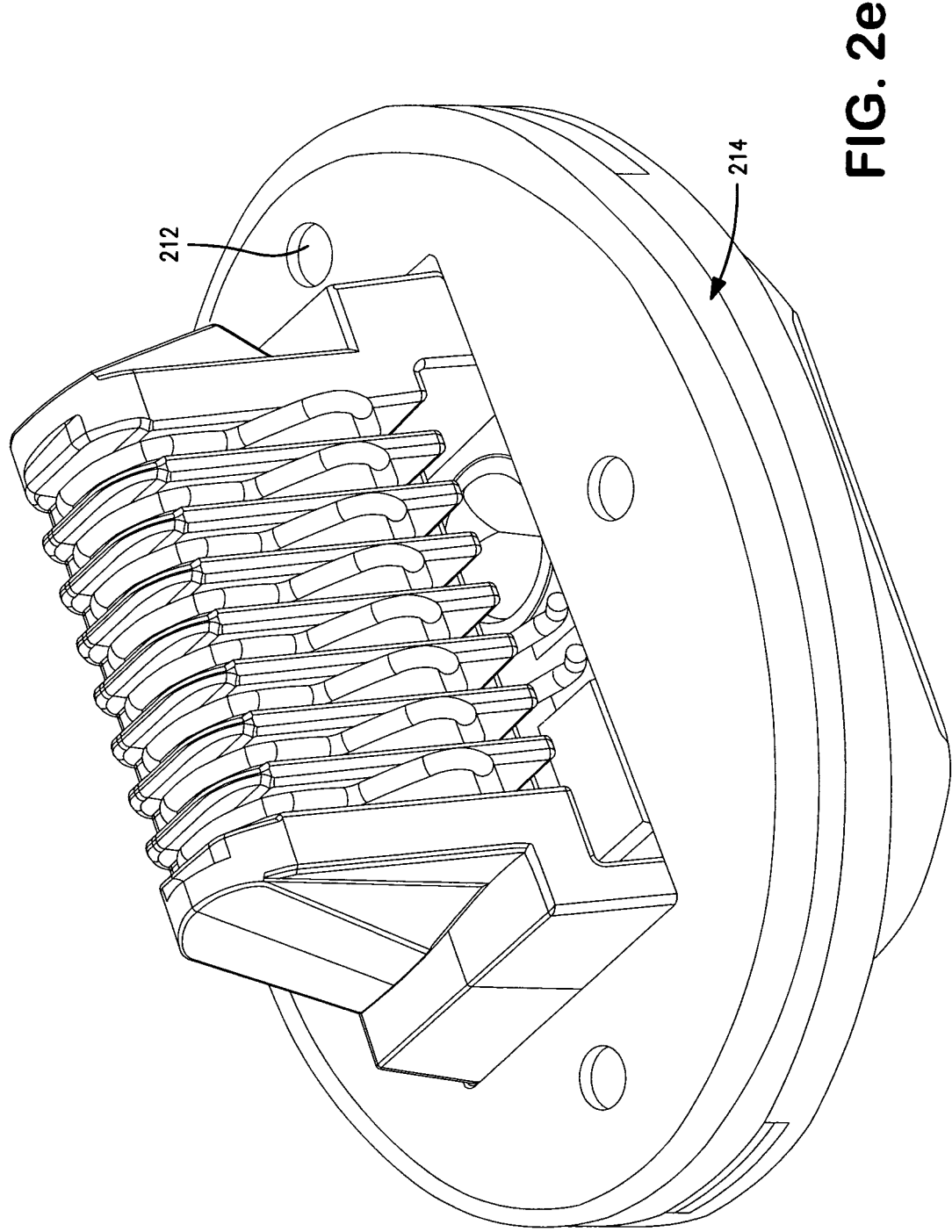
FIG. 2e is an illustration of the exemplary embodiment of the sensor connector assembly placed in the connector housing and encapsulated by the upper encapsulation.

FIG. 2e demonstrates the placement of the final layer of the example multi-layer housing element 214. This layer of the housing element 214 further includes a plurality of coupling indentions 212a, 212b, 212c which are adapted to cooperate in coupling the sensor connector assembly 202 to its parent actuator 300 (described in greater detail with respect to FIGS. 3-3d herein). It is appreciated that different configurations and number of coupling mechanisms may be utilized to facilitate mating of the sensor connector assembly 202 with the actuator 300.

Referring again to FIG. 2a, the biasing element 216 of the sensor connector assembly 202 surrounds the outer/bottom edge portions of the multi-layered housing element 214 as well as the portion of the pressure sensor element (not shown) which will come into contact with the subject's skin. The biasing element 216 is, in one embodiment, made wholly from a silicone-based encapsulation material. There are at least two distinct advantages of using encapsulation material as the biasing element 216 for smaller embodiments such as the sensor connector assembly 202 of FIGS. 2 and 2a. First, the use of encapsulation material eases fabrication, as smaller size foam is more difficult to handle in production environments. Second, the bottom edge of the biasing element 216 can now have a radius or other transitional shape molded into the profile, reducing the size of the shearing effect on the skin as the sensor connector assembly 202 is pressed into the skin during lateral and proximal movements. It will be noted also that the otherwise "unitary" encapsulation material shown may also be comprised of two or more independent or coupled component moldings if desired.

It will also be appreciated that consistent with other embodiment(s) of the sensor assembly 200, other schemes may be used with the invention, such as not using the sensor connector assembly 202 as the applanation element. For example, an actuator coupled to an applanation element (not shown) separate or otherwise decoupled from the pressure or other sensor(s) may be employed. While significant economies and advantages relate to the exemplary use of the sensor as the applanation element, this is by no means a requirement for practicing the invention. Hence, the present invention should in no way be considered limited to embodiments wherein the sensor (i.e. the sensor connector assembly 202) also acts as the applanation mechanism.

While the biasing element 216 in the present embodiment comprises a silicone rubber based compound that is applied over the active face of the pressure transducer (and selective portions of the housing element 214) to provide coupling between the active face and the subject's skin, other materials which provide sufficient pressure coupling, whether alone or in conjunction with an external coupling medium (such as a gel or liquid of the type well known in the art) may be used as well. Further, in some embodiments, it may be desirable to construct the biasing element from, or coat it with, materials having low coefficients of friction such as e.g. Teflon™, etc.

Moreover, the bias element need not necessarily be uniform in material construction, but rather could be constructed using hybrid materials integrated to perform the desirable functions of the bias element when used in combination. This may include mixing materials, doping the silicone material to provide other desirable properties, coating the material (as previously described), and so forth. Myriad other design choices would be readily apparent to those of ordinary skill given the present disclosure.

In the exemplary embodiment, the bias element 216 is formed by molding the encapsulant (e.g., silicone compound) around the sensor element (not shown) and housing element 214 after the sensor (not shown) has been placed in the housing 214. This ensures that the encapsulant completely covers the sensor, and fills all voids. In effect, the bias element 216 is molded around the sensor (not shown), thereby ensuring a conformal fit and direct coupling between the encapsulant material and the sensor's active face. It will also be recognized that the sensor and applanation element configuration of FIG. 2a is merely exemplary, and other sensor configurations (e.g., single or multiple transducer, homogeneous or heterogeneous sensors (i.e., combined with the same or other types of sensors), and/or using different bias element geometry) may be used consistent with the present invention.

Figure 2F:
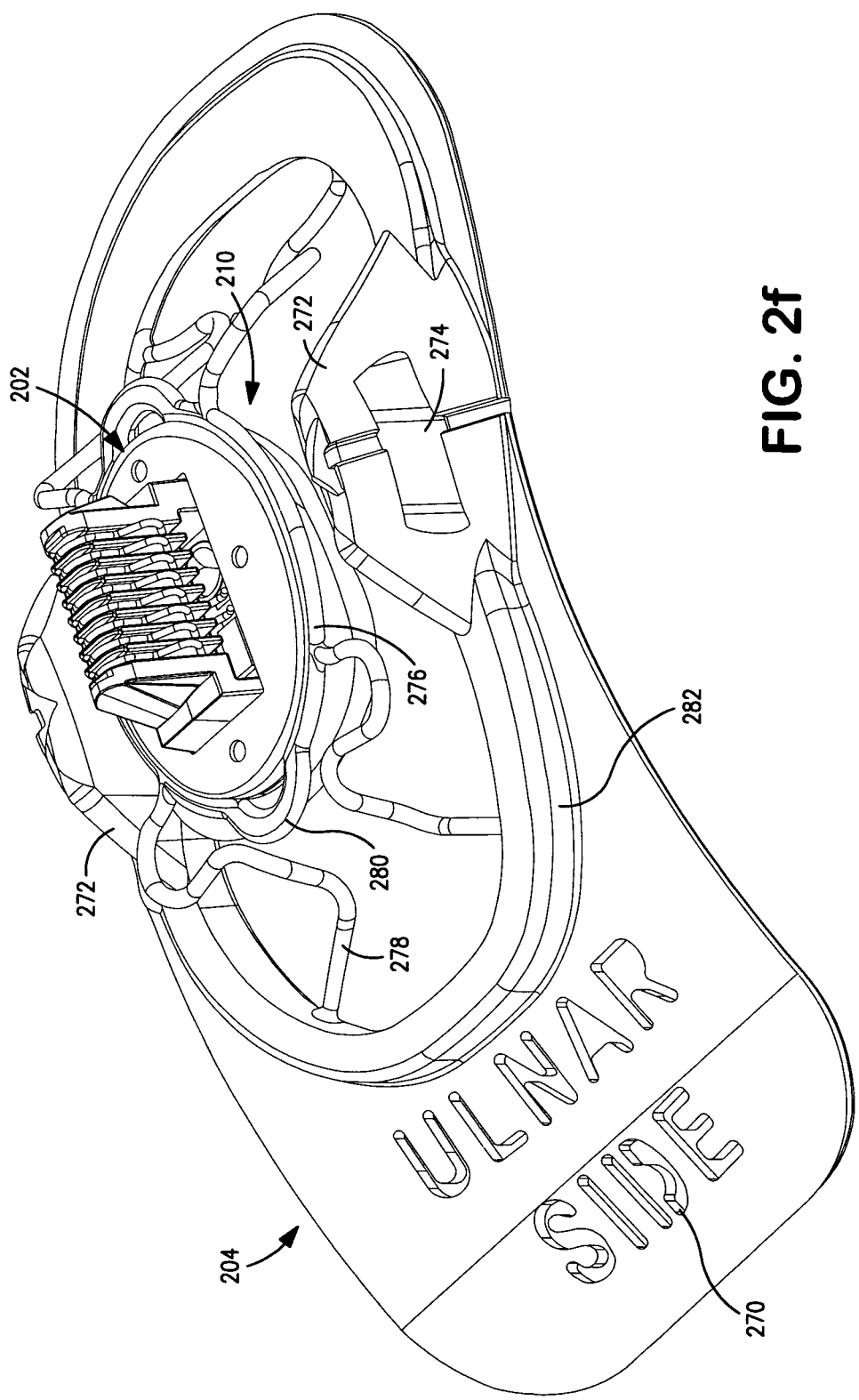
FIG. 2f is an illustration of one exemplary embodiment of the sensor connector assembly mounted in the flexible frame.

FIG. 2f depicts the sensor/applanation element 210 and its connector assembly 202 mounted movably within the flexible frame element 204. This exemplary embodiment generally comprises a single frame element 204, which is distinguished over prior art implementations having two frame elements. This approach advantageously simplifies the construction of the apparatus, and also provides opportunities for reducing manufacturing cost while also increasing ease of use by the caregiver or subject being monitored.

The single frame element 204 comprises a generally planar (yet curved), thin profile. This approach (i.e., flatter and thinner material) has significant advantages over the prior art including allowing for increased conformity and adaptation to the anatomy of the subject being monitored. The single frame element 204 is advantageously shaped from a polymer molding formed from polypropylene or polyethylene, although other materials and degrees of flexibility may be used consistent with the principles of the present invention.

The Assignee hereof has also found through experimentation that placing the sensor at a more distal location with respect to the wrist and forearm can result in more consistent system performance and better accuracy. Thus, in the embodiment shown in FIG. 2f the frame 204 of the apparatus is notably smaller in surface area with respect to the portion of the frame 204 that extends on the radial side of the apparatus when it is disposed on a human subject. Utilizing a shape with a minimized frame in this area permits the apparatus to be placed at a more distal location while avoiding the thenar eminence (the body of muscle on the palm of the human hand just beneath the thumb). It is noted however that the aforementioned level of flexibility of the frame 204 is further selected to permit some deformation and accommodation by the frame to the shape and radius of the wrist of the subject as well. Accordingly, the foregoing optional features coordinate to provide a more comfortable and well-fitted frame and sensing apparatus, thereby also increasing accuracy of the measurements obtained thereby.

Also illustrated in FIG. 2f, the exemplary embodiment of the frame 204 presents the user with a miniature placement "map" by way of the graphic illustration of the location of local physiology through labeling and the like. For example, at one end of the frame element 204, the lettering "ulnar side" 270 is produced by way of cutout on the frame element 204, although other approaches such as labels, painting/marking, etc. may be used to accomplish this function. This phrase refers the user to the fact that this ulnar side of the frame element should be positioned on the ulnar side of the patient's forearm. The cut-through design of the illustrated embodiment is advantageous in that the lettering can be more legible to a user of a device than other approaches, and cannot be removed or fall off. After proper placement, the user then deforms the frame 204 around the subject's wrist, thereby adhering the frame 204 in place on the patient's forearm using an adhesive placed on the contact (skin) side of the frame and exposed after its protective sheet is removed.

Also depicted in FIG. 2f, a set of ribs or risers 272 are provided; these ribs 272 are notable as they are received within corresponding features (e.g., cavities) present on the actuator 300. The embodiment of FIG. 2f advantageously simplifies the design and molding of the alignment apparatus frame 204, as compared to prior art embodiments which utilize complex structures that fit both within and outside of actuator cavities. The ribs 272 are further adapted to comprise an intrusion or aperture 274 on the outer surface of each with respect to the sensor connector assembly 202. The intrusions 274 are adapted to receive complementary tabs 322 associated with the actuator 300 thereby allowing the actuator 300 to be set in place (i.e. mated with the sensor assembly 200) and unable to significantly rotate. Note that in the illustrated embodiment, there is 10° rotation built in to allow for the shape variation in the forearms of different subjects. Once the device is rotated beyond that limit the sides of the cavities press against the sides of the snap features on the actuator and that forces the frame to deflect which releases the frame from the actuator. To install the actuator onto the frame one must simply press the actuator down onto the frame at which point the whole frame acts as a snap fit and latches to the actuator.

This feature ensures an easily formed, robust, and uninterrupted connection of the actuator 300 to the sensor assembly 200.

As demonstrated in FIG. 2f, coupling of the sensor connector assembly 202 to the frame element 204 in the exemplary embodiment is accomplished using a flexible and resilient serpentine-like suspension loop 276 and associated suspending arms 278.

The suspension loop 276 is attached to the circumference of the multi-layered housing element 214; the loop substantially encircles the sensor connector assembly 202 and fits within a groove formed in the outer edge of the sensor element 210, although other arrangements may be used. As illustrated in the figure, sections of the suspension loop 276 are formed so as not to be in contact with the housing element 214 as previously described. These sections form arches 280 which receive the pins 314 located within the actuator receptacle 304 when the actuator 300 is mated with the sensor assembly 200. However, other methods for assisting and maintaining the sensor connector assembly 202 within the actuator receptacle 304 may be used with equal success.

Note that in the illustrated embodiment, the end loops also facilitate putting the elliptical ring feature of the suspension loop around the groove of the sensor multi-layer assembly. They allow the ring to "stretch" for assembly.

The suspending arms 278 are coupled rigidly to the frame element 204 via integral injection molding, adhesive or other means and attached flexibly to the suspension loop 276. The suspending arms 278 in the present embodiment provide sufficient "slack" such that the frame element 204 and the sensor element 210 can move to an appreciable degree laterally (and in other degrees of freedom) within the frame 204, thereby allowing the actuator 300 to move the sensor element 210 relative to the radial artery during execution of its positioning algorithm and automatic zeroing of the sensor. The present invention also allows for such freedom of movement in the proximal direction as well as in the direction of applanation or blood vessel compression. Moreover, sufficient slack may be provided in the suspending arms 278 to allow a desired degree of proximal movement of the sensor element 210 by the actuator 300, as well as rotation of the sensor element in the X-Y plane (i.e., "yaw" of the sensor assembly about its vertical axis). Other arrangements may also be used, such alternatives being readily implemented by those of ordinary skill in the mechanical arts.

It will be further noted that in the illustrated embodiment, the suspension loop 276 and associated suspending arms 278 maintain the sensor element 210 (including most notably the active surface of the assembly) in a raised position completely disengaged or elevated above the surface of the skin. This advantageously allows the operator and the system to verify no bias of the sensor and pressure transducer during periods when bias is undesirable, such as during calibration of the sensor.

The exemplary zeroing algorithm includes various features, including (i) checking for a quiescent state wherein the output from the sensor is steady (e.g., monotonic, although not necessarily constant, due to e.g., sensor warmup or other temperature effects), which does not happen when the sensor is touching skin, and/or (ii) retracting the sensor up into the actuator and "dithering" the applanation position in order to ensure that if the pressure does not change the sensor is truly off the skin. Either or both of these approaches may be used.

FIG. 2*f* also depicts an exemplary frame lip 282 which is formed along the circumference of the central aperture of the frame element 204. The frame lip 282 is designed to fit snugly within the actuator receptacle 304 thereby holding the sensor assembly 200 in contact with the actuator 300. The lip also adds rigidity to the frame in the direction in which the snap fits act for the attachment of the frame to the actuator. It also prohibits the actuator from being placed on backwards by interfering with features on the opposite side of the actuator.

Thus the actuator receptacle 304, as discussed below, is comprised of a "moat" to accept the protruding frame lip 282. The frame lip 282 configuration of the exemplary embodiment is preferable to other prior art configurations because, inter alia, this configuration permits a single-step, unobstructed connection of the sensor assembly 200 to the actuator 300. There is also better automatic guidance, thereby minimizing the chance of a mismatch.

Figure 2G:
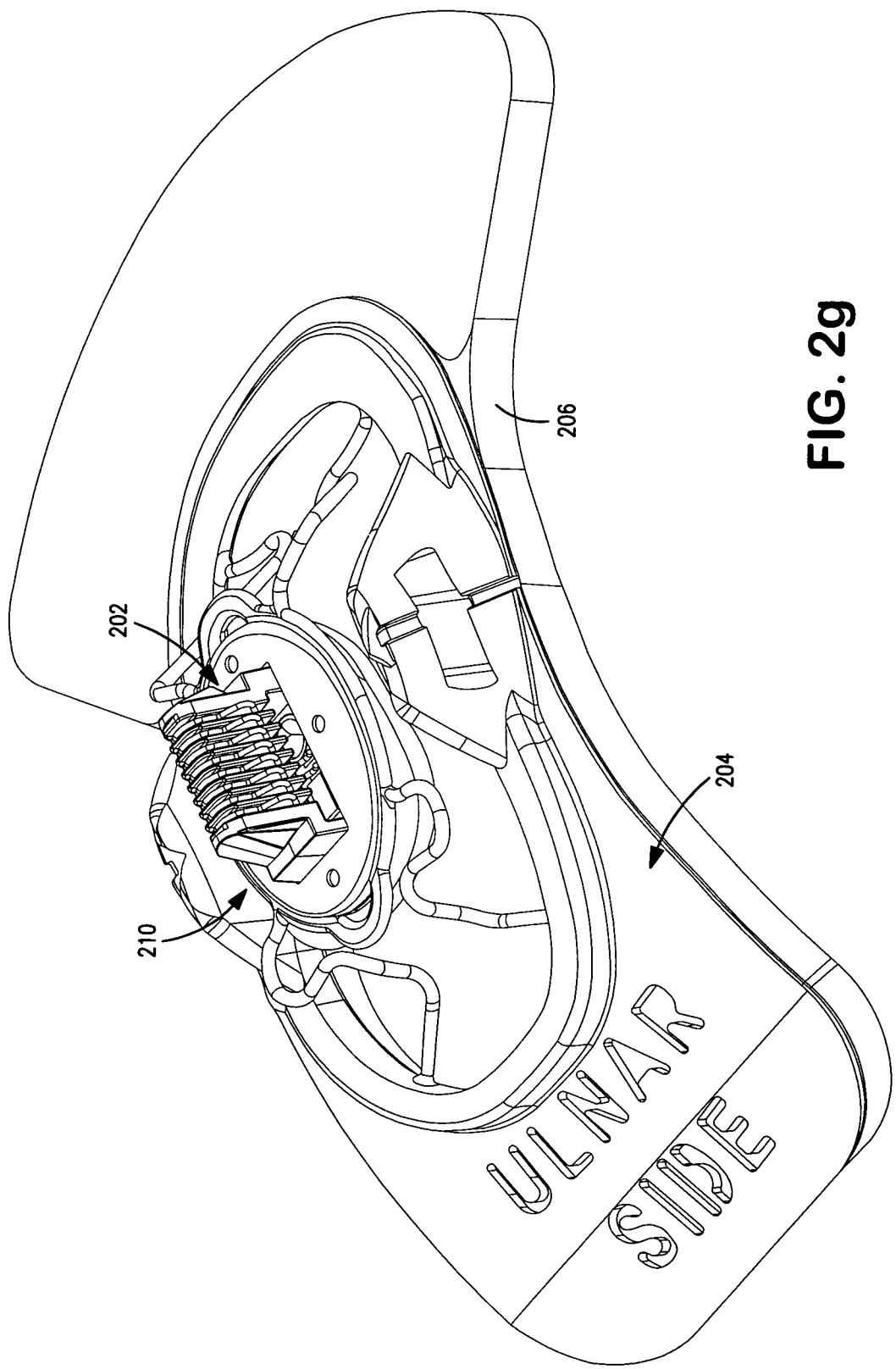
FIG. 2g is an illustration of one exemplary embodiment of the sensor connector assembly and frame mounted on a foam backing.

Referring now to FIG. 2*g*, the foam backing 206 onto which the frame element 204 is disposed is described in detail. The foam backing 206 is comprised of compliant foam with adhesive surfaces that is mounted to the contact-side of the element 204. The foam backing can advantageously be conformed to the unique profiles and shapes associated with living subjects of varying shapes and sizes.

As described above, the frame element 204 is substantially minimized with respect to the radial portion in this embodiment as compared to prior art embodiments. Accordingly, the foam backing 206 may be adapted to extend the radial portion of the sensor assembly 200 in order to permit increased surface area for attachment to a subject. As discussed above, the shape of the foam backing 206 will be such that the thenar eminence ("thumb muscle") of a human subject continues to be accommodated. Thus, the attachment of the sensor assembly 200 is not obstructed, but rather conforms to the natural raises and indentations in a subject's anatomy.

The adhesive on the underside of the compliant foam backing 206 is adapted such that when the frame element 204 is disposed atop the subject's skin, it bonds to the skin, the frame element 204 deforming somewhat to match the surface contour of the skin. The adhesive is selected so as to provide a firm and long-lasting bond (especially under potentially moist conditions resulting from patient perspiration, etc.), yet be readily removed when disposal is desired without significant discomfort to the subject. However, other means for maintaining the frame element 204 in a constant position with respect to the subject's anatomy may be used, including for example Velcro straps, tape, application of an adhesive directly to the underside of the frame element 204 itself, etc. In another embodiment, a thermally- or light-sensitive frame material is used that allows the initially deformable and pliable frame element to become substantially more rigid upon exposure to heat, light, or other such "curing" process.

A low-cost removable backing sheet (e.g., waxed or coated on one side) of the type well known in the adhesive arts may be used to cover the aforementioned adhesive (not shown) disposed on the interior or contact side of the frame element 204 prior to use, so as to preclude compromise thereof. The user simply peels off the backing sheet, places the frame element 204 on the desired anatomy location, and gently compresses it against the subject's skin to form the aforementioned bond, deforming the frame element 204 as needed to the contour of the subject's anatomy. The adhesive bond is strong enough, and the frame element pliable enough, such that any deformation of the frame element is substantially preserved by the bond as discussed above.

As discussed above, a notable difference between the foregoing exemplary embodiment of the sensor assembly 200 described above and that of the prior art is the absence of a "paddle" element in the present invention. The paddle element is used in the prior art to place the sensor assembly in a desired location relative to the subject's anatomy. In the present invention, however, the necessity for the user to place the sensor assembly manually is obviated in favor of an automatic zeroing process. In this embodiment, the automatic zeroing advantageously simplifies the operation of the apparatus, and also provides opportunities for reducing manufacturing cost, because there is no need to manufacture a paddle, assemble it, and so forth. Rather than aligning the artery or other blood vessel between the two parallel lines of the paddle (e.g., by aligning the longitudinal axis of the target portion of the artery between the two parallel features of the reticle), the present invention permits a user to merely place the apparatus on the subjects anatomy, and line up the arrow marks on the sides of the frame with the line of the artery. Further, the straight edges of the frame are supposed to line up with the "wrist break" where the wrist ends and the hand starts. The shape of the foam is also supposed to seat the frame in close proximity to where it is needed due to the flare shape which simulates the thump flaring to one side. Thus, the present invention greatly increases the ease of use by the caregiver or subject being monitored.

In the illustrated embodiment, the substantially elliptical sensor shape also accommodates moving the edge of the frame 204 closer to the centerline of the apparatus, so that the frame 204 can accommodate the thenar eminence. The reduced sensor size and profile in the lateral/medial direction (as compared to other embodiment described herein) also allows the frame to be smaller than it otherwise would, and the sides of the sensor impinge less on tendons that run in the proximal/distal direction.

Moreover, by making the sensor smaller in all directions, the surface area being pressed into the skin is reduced, which reduces the power needed to drive the sensor into the skin. By reducing the power required, the applanation/positioning mechanisms can be made smaller, and less electrical power is required (important for "stand-alone" or battery powered variants).

Another advantage of the smaller elliptically-shaped sensor element 210 is that because of the reduced lateral/medial length, the sensor impinges less on tendons during sensor travel (e.g., in the lateral/medial direction) as previously noted, thereby allowing the sensor to slide across the surface of the skin in a more uniform and smooth manner.

This provides enhanced performance during, inter alia, lateral search phase monitoring. In addition, the elliptical shape of the sensor 210 of FIGS. 2-2g provides a continuously curved surface on the outer periphery of the sensor connector assembly 202, facilitating movements in both the lateral and proximal axes by reducing shear effects. Specifically, in one aspect, the elimination of "corners" on the elliptical variant makes changes in direction and movement smoother in all directions, and when coupled with the curved sidewall or cross-sectional profile of the assembly, allows for some degree of roll, pitch, and/or yaw of the sensor relative to the tissue surface (or conversely, greater irregularities within the tissue shape or surface) without adversely impacting movement of the sensor assembly across the tissue.

Figure 3:
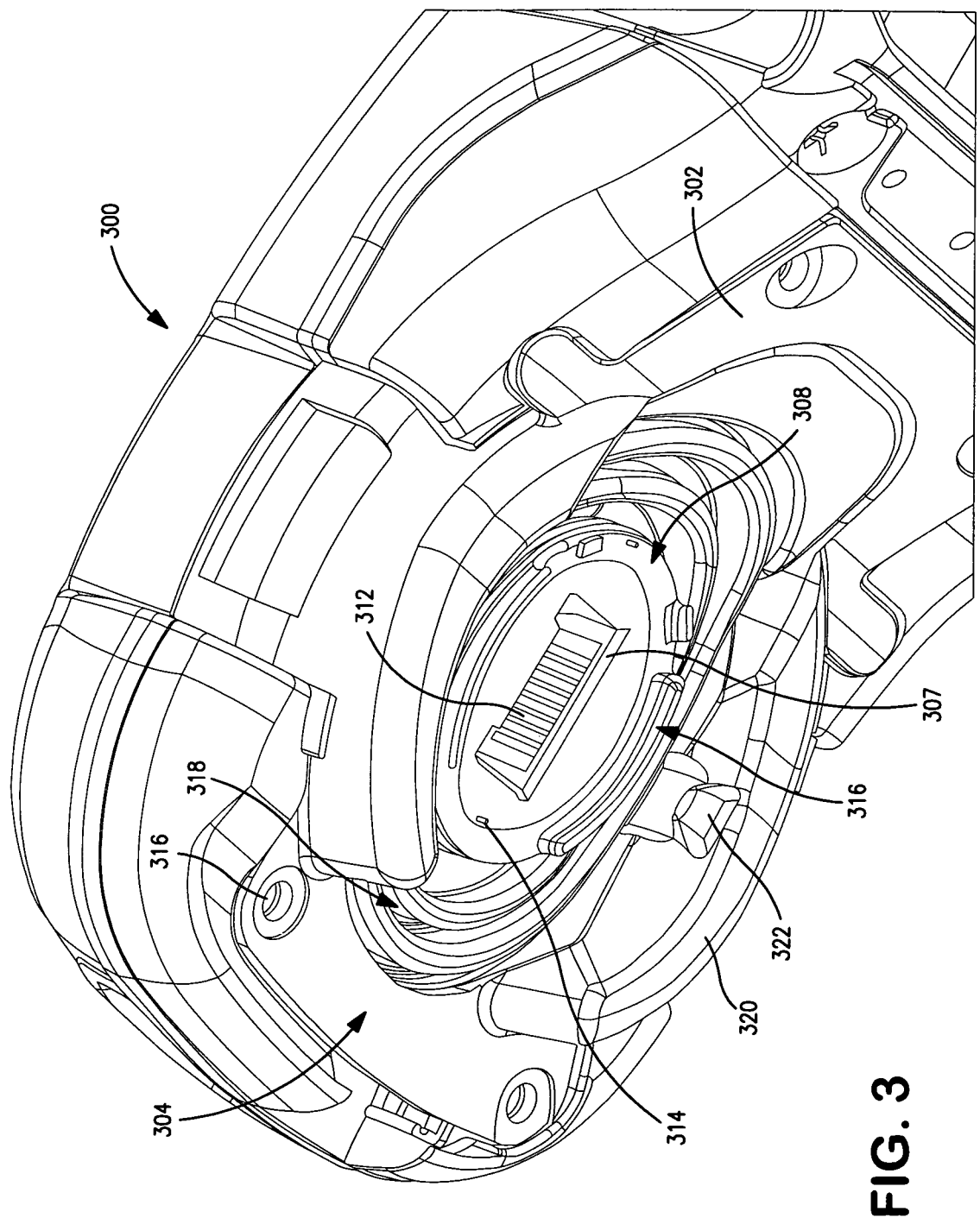
FIG. 3 is a perspective view of the underside of one exemplary embodiment of the actuator element illustrating the connector and sensor attachment plate.

Referring now to FIGS. 3-3d, one exemplary embodiment of the actuator assembly 300 of the invention is described. The actuator 300 described herein is designed to provide adjustment or movement of the position of the sensor element 210 in both sagittal and lateral (transverse) directions; however, it will be appreciated that it may be modified to provide more or less degrees of freedom (including, for example, proximal adjustment). Hence, the following embodiments are merely exemplary in nature.

FIG. 3 illustrates the underside of one embodiment of the actuator assembly 300. The underside of the actuator in this embodiment is generally comprised of an attachment plate 302 onto which various coupling mechanisms and receiving apparatus are disposed. The receiving apparatus (e.g. the actuator receptacle 304, the connector disk 310 and connector recess 308) provide cavities within which portions of the sensor connector assembly 202 are accepted when the sensor element 210 (and assembly 200) and the actuator 300 are mated. The coupling mechanisms (e.g. the frame lip receiving walls 320 and complementary tabs 322, and the actuator receptacle rings provide a secure connection between the actuator 300 and the sensor connector assembly 202. A rubber bellows 318 is also provided that allows the receptacle to move with respect to the rest of the actuator and seals the opening around the receptacle from fluid or dirt ingress. Each of these features will be discussed in detail below. It will be recognized, however, that other coupling arrangements for the secure mating of the actuator 300 to the sensor element 210 and assembly 200, whether utilizing the coupling mechanisms and receiving apparatus or not, may be employed consistent with the invention.

The exemplary attachment plate 302 further comprises a plurality of plate attachment features by which the attachment plate is fastened to the underside of the actuator 300. In the exemplary embodiment of FIG. 3, the plate attachment features consist of threaded cavities which are designed permit assembly via screwing the attachment plate into the actuator 300 body. It is appreciated that other methods and techniques may be utilized to secure the attachment plate 302 to the actuator 300 body, such as, for example, via a glue, latch, or similar technique.

In the exemplary embodiment, the underside of the actuator 300 features an actuator receptacle 304. The actuator receptacle 304 is a recess in the actuator plate 302 which is adapted to receive the sensor assembly 200. The actuator receptacle 304 is comprised of a plurality of inner rings, a connector disk 310 and frame lip receiving walls 320.

The connector disk 310 is adapted to accept portions of the sensor connector assembly 202 and promote secure mating therewith. Accordingly, the connector disk 310 comprises a partial bearing ring 316 which conforms substantially to the corresponding features of the sensor connector assembly 202 and helps secure the actuator 300 in place, especially under conditions of transverse loading or rotation of the actuator 300 around the lateral or proximal axis. The connector disk 310 also comprises a plurality of pins 314 which fit into the arches 280 of the suspension loop 276. As described previously, when the actuator 300 is mated with the sensor assembly 200, the pins 314 will be received snugly within the aperture created by the suspension loop arches 280.

The connector recess 307 is disposed on the connector disk 310 of the actuator receptacle 304. The connector recess 307 is specifically adapted to accept the pyramidal sensor connector 218. Thus, it consists of an inverted pyramidal shaped recess. The inverted pyramidal shaped recess of the connector recess 307 is further adapted to maintain electrical contact with the plurality of wires 220 on the sensor connector 218 when the two 307, 218 are mated. This electrical communication occurs via placement of electrical contacts 308 on the connector recess 307 by which electrical signals are transmitted. The receptacle also has a "U" shape that precludes the connector from being put in backwards.

FIG. 3 further illustrates the frame lip receiving walls 320, which are disposed on the actuator receptacle 304. The frame lip receiving walls 320 conform substantially to the corresponding features of the frame element 204 and help secure the actuator 300 in place. Specifically, the frame lip receiving walls 320 create a moat wherein the ribs or risers 272 of the frame element 204 are fitted when the actuator 300 and sensor assembly 200 are mated. The frame lip receiving walls 320 are further adapted to include complementary tabs 322 which are designed to snap into the matching intrusions 274 on the ribs 272, thereby allowing the actuator 300 to be set in place (i.e. mated with the sensor assembly 200) and unable to rotate. When viewed from the side the receiving walls also have a shape that precludes the actuator from being put on backwards.

FIGS. 1 and 3a-3c illustrate the exemplary coupling between the actuator 300 and sensor assembly 200. As best illustrated in FIG. 1, the various coupling mechanisms (described above) are configured so as to mate the actuator 300 and sensor assembly 200 together in a unitary (but readily separable) assembly.

Figure 3A:
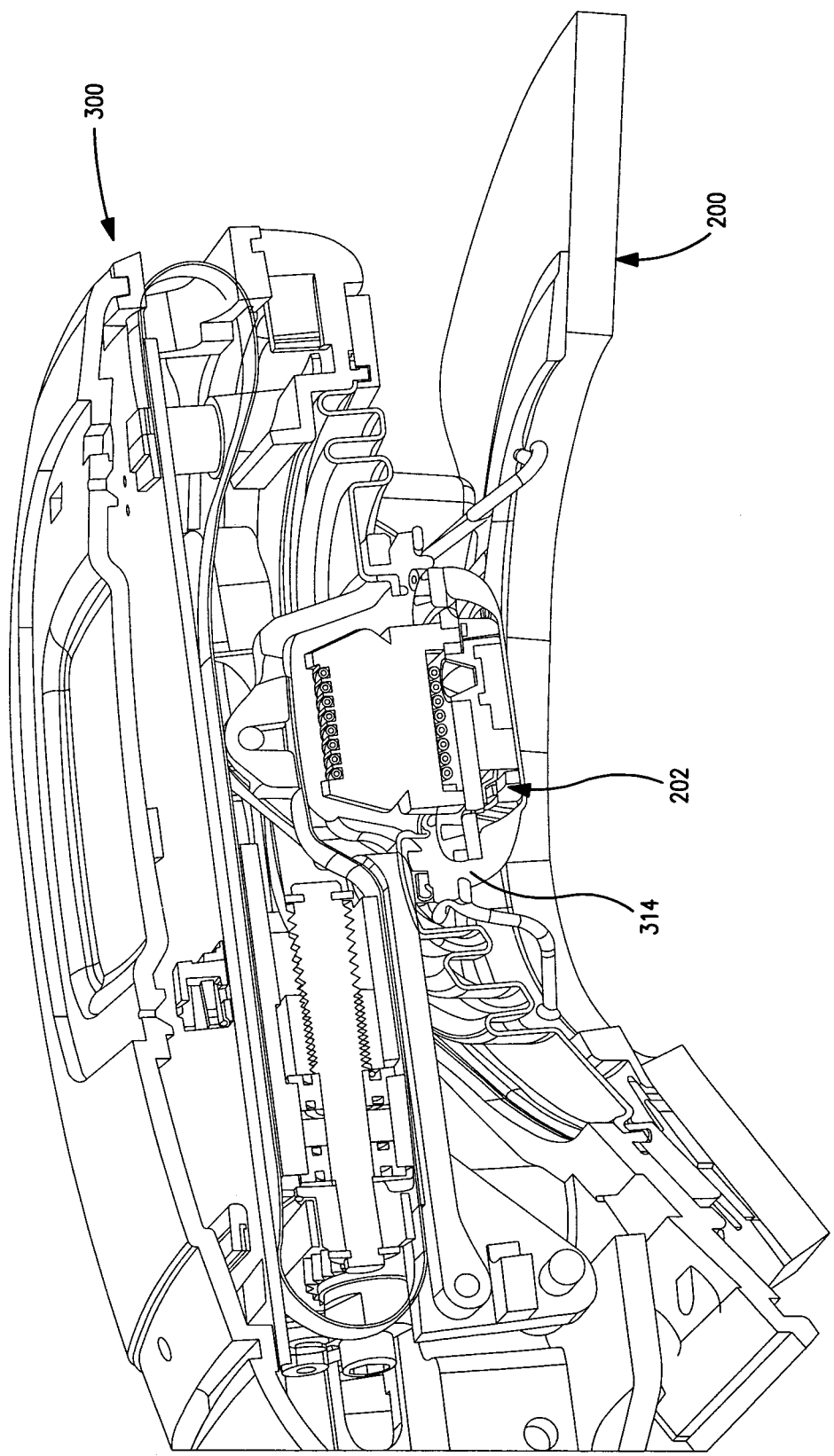
Figure 3B:
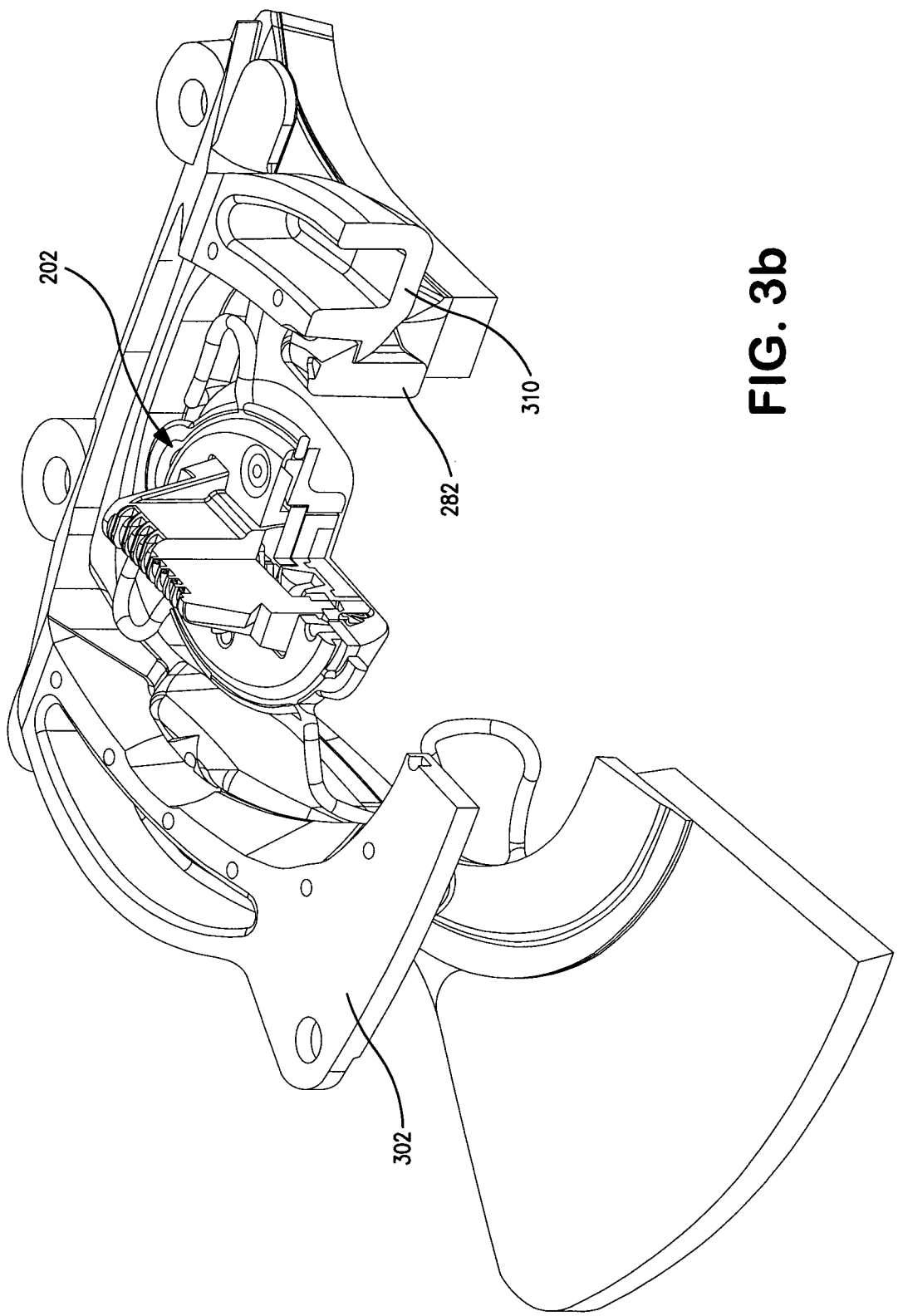
Figure 3C:
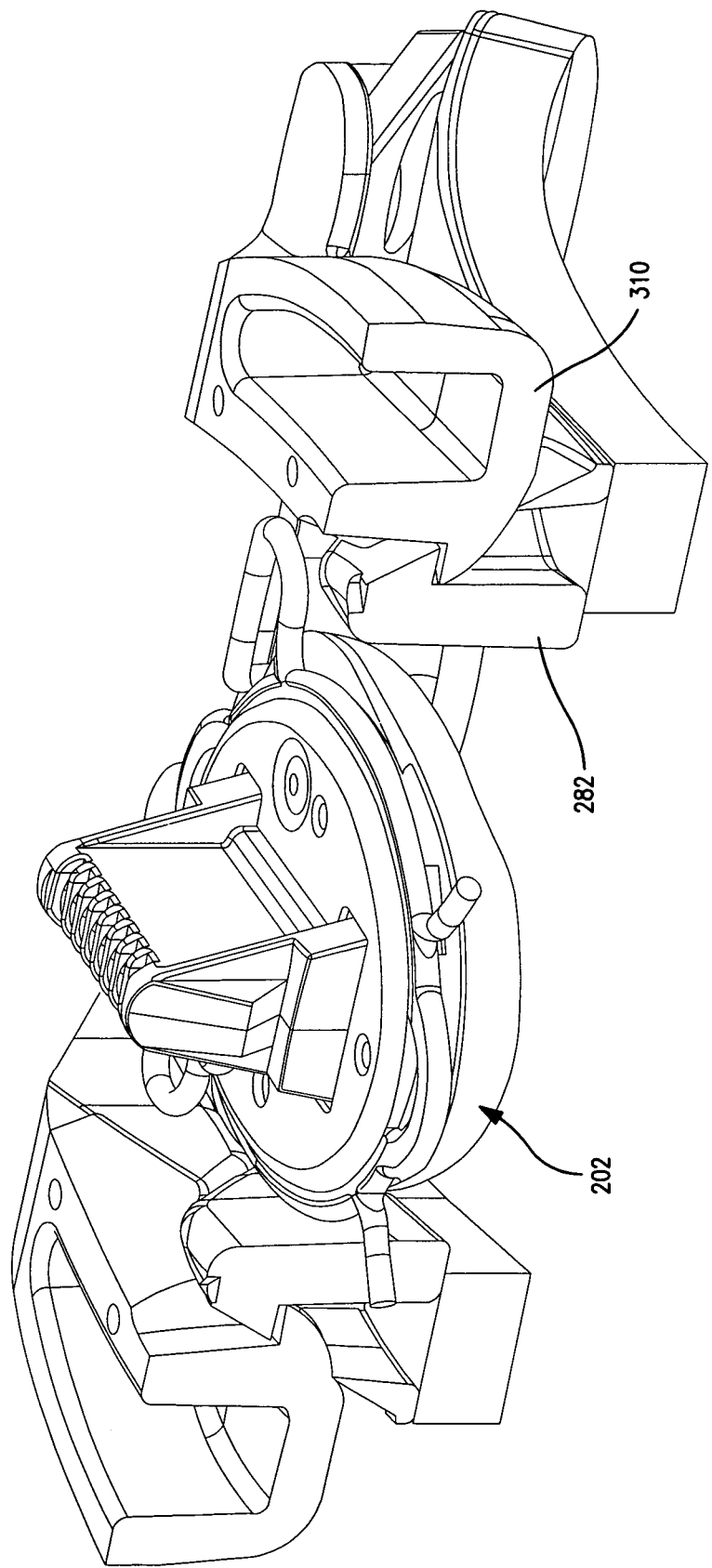
FIG. 3c is a cut-away view of the exemplary embodiment of the sensor assembly mated with the attachment plate of the actuator.

Referring to FIGS. 3a-3c, in the illustrated embodiment, the top of the sensor connector assembly 202 is substantially elongated pyramidal in shape due to the pyramidal shaped sensor connector 218. Similarly, the connector recess 308 attached to the actuator 300 is effectively the inverse of the sensor connector assembly 202 in shape; i.e., it is adapted to generally match the contours of the sensor connector assembly 202 and the alignment and retention features almost exactly. Hence, portions of the sensor connector assembly 202 which are received into the actuator 300 can be considered the "male" element, while the connector recess 308 is considered the "female" element. The substantially square shape of the base of the sensor connector 218 aids in controlling rotation of the connector recess 308 with respect to the sensor assembly 200 under torsional load. This coupling of the two elements 218, 308 allows for a highly rigid and non-compliant joint between the actuator and sensor assembly in the applanation (normal dimension), thereby effectively eliminating errors in resulting hemodynamic measurements which would arise from such compliance. This design, however, also includes enough tolerance between the coupling components to facilitate easy decoupling of the sensor assembly 200 from the actuator 30. The serpentine like suspending arms 278 provide more than sufficient strength to prevent separation of the sensor connector assembly 202 from its parent sensor assembly 200 while still permitting movement therein; the sensor assembly 200 is specifically configured such that, under all attitudes, the sensor connector assembly 202 will separate from its coupling to the actuator 300 well before the serpentine arms 278 yield significantly.

It will be noted that the elongated pyramid shape of the coupling elements further allows for coupling of the two devices under conditions of substantial misalignment; i.e., where the apex of the sensor connector assembly 202 is displaced somewhat in the lateral (i.e., X-Y) plane from the corresponding connector recess 308 of the actuator 300, and/or the sensor assembly 200 is rotated or cocked with respect to the actuator 300 prior to coupling. This feature aids in ease of clinical operation, in that the instrument can tolerate some misalignment of the sensor and actuator (the latter due to, e.g., the actuator arm of the actuator 300 (not shown) not being in perfect alignment over the sensor assembly 200 and sensor element 210).

It will further be recognized that while the illustrated embodiment comprises elongated substantially pyramid-shaped elements, other shapes and sizes may be utilized with success. For example, the apparatus may comprise complementary conic or frustoconical sections. As yet another alternative, a substantially spherical shape could be utilized. Other alternatives include use of multiple "domes" and/or alignment features, inversion of the first and second elements (i.e., the first element being substantially female and the second element being male), or even devices utilizing electronic sensors to aid in alignment of the two elements.

In one embodiment of the hemodynamic assessment apparatus 100 of the invention, the apparatus is adapted to notify the user/operator of the presence of the sensor assembly (as well as the status of its coupling to the actuator 300 and the sufficiency of electrical tests of the sensor assembly) through an integrated indication. Any type of indication scheme well known to those of ordinary skill in the electronic arts may be used, including for example one or more single color LED which blinks at varying periods (including no blinking) to indicate the presence or status of the components, such as by using varying blink patters, sequences, and periods as error codes which the operator can use to diagnose problems, multiple LEDs, light pipes. Optionally, the device further comprises a circuit which evaluates parameters in the pressure transducer and thereby can determine if the connection has been made to the transducer and EEPROM. The device may also be configured to look for the information in the EEPROM to know if it is connected if desired.

FIG. 3a is a cross sectional view of the actuator 300 coupled to the sensor assembly 200. Specifically, the illustration demonstrates the electrical and mechanical connector of the sensor connector assembly 202 within the connector recess 308.

The break-away view depicted in FIG. 3b further demonstrates the precise cooperation between the sensor connector assembly 202 and the attachment plate 302. The interaction of the frame lip 282 (of the frame element 204 of the sensor assembly 200) and the frame lip receiving walls 320 is shown. However, a more detailed depiction of this interaction is available in FIG. 3c.

FIG. 3c, as discussed above, is an illustration of the latching mechanism of the frame lip 282 and receiving walls 320. As shown best in FIG. 3, the underside of the actuator 300 is also configured to include two ridges or walls 320 with complementary tabs 322. As shown in FIG. 2f, the sensor assembly 200 is configured to include risers or ribs 272 with corresponding intrusions 274. The tabs 322 of the actuator 300 fit within the intrusions 274 of the sensor assembly 200 as shown. The snaps on the attachment plate do indeed snap into the recesses in the sides of the frame ribs (element 322 fits into element 274), As shown best in FIG. 3, the underside of the actuator 300 is configured to include two ridges or walls 320. As shown in FIG. 2f, the sensor assembly 200 is configured to include a frame lip 282. The frame lip does not interlock with anything in the actuator; rather it sits below the actuator. The frame lip also make the frame stiffer in that area which improves the snap of the latching tabs on the underside of the actuator to the frame.

The interior components (not shown) of the actuator 300 will be of the type described in Assignee's co-pending U.S. patent application Ser. No. 10/961,460 entitled "Compact Apparatus and Methods For Non-Invasively Measuring Hemodynamic Parameters" filed Oct. 7, 2004, which Assignee hereby incorporates by reference in its entirety. These generally comprise, inter alia, a motor chassis assembly with associated sensor drive coupling, and substrate (e.g., PCB) assembly.

It will further be recognized that an exemplary embodiment of the actuator mechanism would allow for the separation of the movement of the sensor connector assembly in the various directions; i.e., applanation, lateral, and proximal. Specifically, the actuator mechanism would permit concurrent yet independent movement in the various directions, as well as allow for a highly compact and space/weight efficient actuator. An exemplary actuator mechanism would further be adapted so as to minimize the number of components within the actuator (including the motors), thereby reducing electrical power consumption as well as any effect on pressure measurements resulting from the translation of a mass within the actuator during such measurements.

Methodology

Figure 4:
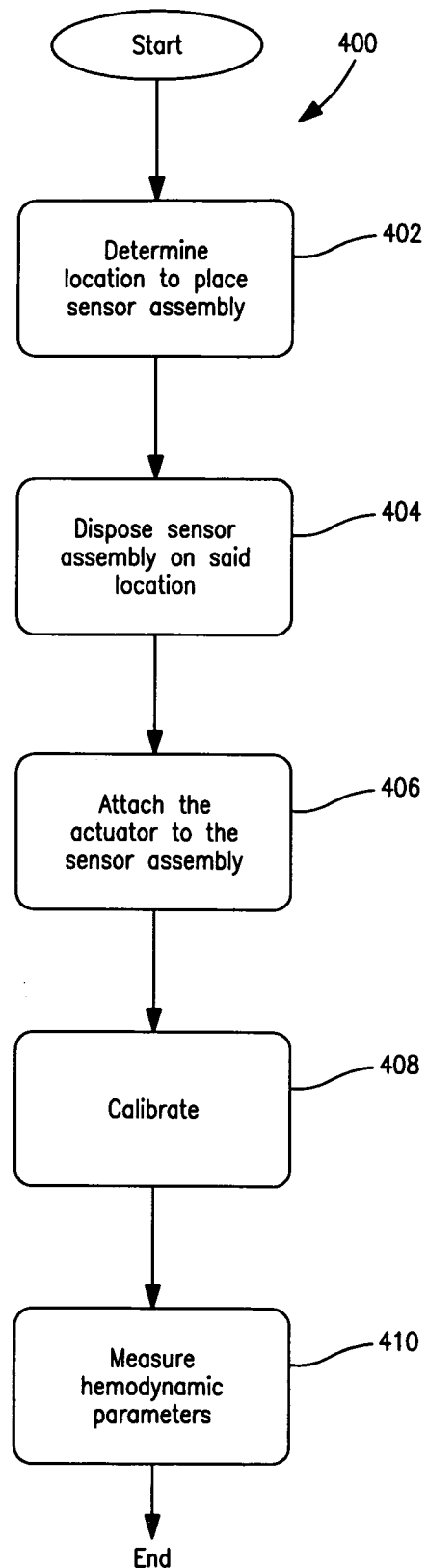
FIG. 4 is a block diagram of the general method by which the hemodynamic assessment apparatus may be utilized.

Referring now to FIG. 4, the general and improved method 400 of positioning a sensor with respect to the anatomy of the subject and recurrently measuring the blood pressure of the subject is now described. It will be recognized that while the following discussion is cast in terms of the placement of a tonometric pressure sensor (e.g., silicon strain beam device) used for measuring arterial blood pressure, the methodology is equally applicable to both other types of sensors and other parts of the subject's anatomy, human or otherwise.

As shown in FIG. 4, the illustrated embodiment of the method 400 generally comprises first determining the location of the anatomy on which the apparatus is to be placed (step 402).

Next, the sensor is disposed relative to the marker (step 404). Specifically, in this step of the method, the user or clinician removes the backing sheet to expose the adhesive on the foam backing 206, and then bonds the frame element 204 to the subject's skin, such that the sensor connector assembly 202 is aligned generally over the pulse point of interest. The sensor is automatically zeroed (e.g., by the zeroing algorithm previously described) once placed on the subject's anatomy, and may also be adjusted laterally and or proximally according to a placement or locating algorithm of the type referenced elsewhere herein, thereby obviating a need for manual precise placement. In the exemplary embodiment, the frame element 204 and sensor connector assembly 202 come "assembled" and pre-packaged, such that the user merely opens the package, removes the sensor assembly 200 (including installed sensor connector assembly 202), and removes the backing sheet from the adhesive and places the frame element 204 as previously described.

As per step 406, the actuator 300 is securely mated with the sensor assembly. In an alternative embodiment, an optional wrist brace is first attached to the subject so as to provide stability to the subject's anatomy. The actuator 300 is then attached to the sensor assembly 200 and wrist brace. As described above, in one embodiment, an indicator will signify when the actuator 300 is properly mated with the sensor assembly 200.

In step 408, the device is "zeroed" and calibrated if required.

Lastly, in step 410, the blood pressure or other parameter(s) of the subject are measured using the sensor(s) subsequent to the calibration (step 408).

Specifically, the sensor position is maintained with respect to the anatomy between measurements using the frame element 204 and adhesive on foam backing 206 as well as the optional wrist brace. These cooperate to maintain the sensor element 210 generally atop the desired pulse point of the subject even after the actuator 300 is decoupled from the sensor. Herein lies a significant advantage of the present invention, in that the actuator 300 (and even the remainder of the hemodynamic monitoring apparatus 100, including brace) can be removed from the subject, leaving the sensor assembly 200 and hence sensor element 210 in place. It may be desirable to remove actuator 300 for example where transport of the subject is desired and the present location has dedicated equipment which must remain, or the monitored subject must have the apparatus 100 removed to permit another procedure (such as post-surgical cleaning, rotation of the subject's body, etc.). The sensor element 210 is maintained effectively constant with respect to the subject pulse point because it is securely attached to the frame element 204 via the suspension loop 276.

Hence, when it is again desired to monitor the subject using the sensor, the bracelet with actuator 300 (or another similar device at the destination), if used, is fitted to the subject. The user/caregiver then merely places the bracelet and presses to attach the actuator 300 to the sensor element 210 (and sensor assembly 200) since the sensor assembly is still disposed in the same location with the frame element 204 as when the first actuator was decoupled. The sensor is automatically zeroed, as described above, accordingly, no use of any alignment apparatus or other techniques for positioning the sensor "from scratch" is needed, thereby saving time and cost. This feature further allows for more clinically significant or comparable results since the same sensor is used with effectively identical placement on the same subject; hence, and differences noted between the first and second measurements discussed above are likely not an artifact of the measurement apparatus 100.

It will be further recognized that while two measurements are described above, the sensor assembly 200 and methodology of the invention allow for multiple such sequential decoupling-movement-recoupling events without having any significant effect on the accuracy of any measurements.

While the foregoing method has been found by the Assignee hereof to have substantial benefits including ease of use and low cost, it will be recognized that any number of different combinations of these or similar steps may be used (as well as different apparatus). For example, it is feasible that the manufacturer may wish to provide the components as a kit, which the user assembles.

As yet even a further alternative, a "marker" may be used in conjunction with the frame. For example, the marker may comprise a tangible marker or sight (e.g., plastic reticle), light source (such as an LED, incandescent bulb, or even low-energy laser light) which is projected onto the desired pulse point of the subject. This latter approach has the advantage point that no physical removal of the marker is required; rather, the sensor assembly 200 can simply be put into place over the pulse point, thereby interrupting the light beam with no physical interference or deleterious effects.

Alternatively, an acoustic or ultrasonic marker (or marker based on a physical parameter sensed from the subject such as pressure) can be employed. The sensor or array may be used to precisely localize the pulse point using for example a search algorithm, such as that described in Assignee's co-pending applications previously incorporated herein, to find the optimal lateral position. This advantageously obviates the need for a reticle or other marker, since the onus is on the clinician/user to place the frame 204 properly within at least the proximal dimension. Such search method can also be extended into the proximal dimension if desired, such by including an actuator with a proximal drive motor, and a broader frame dimension.

Clearly, myriad other different combinations and configurations of the basic methodology of (i) positioning a marker with respect to a point; (ii) disposing a sensor with respect to the marker, and (iii) disposing the sensor proximate the desired point, will be recognized by those of ordinary skill given the present disclosure. The present discussion should therefore in no way be considered limiting of this broader method.

As previously noted, one of the significant advantages of the present invention relates to its flexibility; i.e., that it is essentially agnostic to the hardware/firmware/software on which it is used, and can be readily adapted to various different platforms or systems for measuring hemodynamic or other physiologic parameters. For example, the methods and apparatus of the present invention are substantially compatible with, inter cilia, those described in: co-pending U.S. patent application Ser. No. 10/393,660 "Method and Apparatus for Control of Non-Invasive Parameter Measurements" filed Mar. 20, 2003; co-pending U.S. patent application Ser. No. 10/269,801 entitled "Apparatus and Methods for Non-Invasively Measuring Hemodynamic Parameters" filed Oct. 11, 2002; co-pending U.S. patent application Ser. No. 10/920,999 entitled "Apparatus and Methods for Non-Invasively Measuring Hemodynamic Parameters" filed Aug. 18, 2004; co-pending U.S. patent application Ser. No. 11/336,222 entitled "Apparatus and Methods for Non-Invasively Measuring Hemodynamic Parameters" filed Jan. 20, 2006; co-pending U.S. patent application Ser. No. 09/534,900 filed Mar. 23, 2000 and entitled "Method and Apparatus for Assessing Hemodynamic Parameters within the Circulatory System of a Living Subject" which is now U.S. Pat. No. 6,554,774 issued Apr. 29, 2003, each of the foregoing assigned to the Assignee hereof and incorporated by reference herein in its entirety.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A sensor assembly adapted to sense a hemodynamic parameter from a living subject, comprising:
    a substantially conformal frame; and
    a sensor element, said sensor element being encircled by a flexible and resilient suspension loop and coupled to said frame via one or more suspending arms extending from said suspension loop;
    wherein said sensor element further comprises an electrical interface, and said sensor element is configured so as to form an electrical connection with a corresponding electrical interface of a host device simultaneously during mating of said sensor element to said host device.

2. The sensor assembly of claim 1, wherein said sensor element comprises a blood pressure sensor, and further comprises:
    a biasing element;
    a pressure transducer;
    a plurality of electrical conductors disposed on at least one printed circuit board and adapted to electrically interface with said host device; and
    a housing element adapted to encase at least a portion of said sensor element.

3. The sensor assembly of claim 2, wherein said housing element comprises a substantially pyramid-shaped portion, at least a portion of said electrical conductors being disposed thereon.

4. The sensor assembly of claim 1, wherein said host device comprises an actuator.

5. The sensor assembly of claim 1, wherein said mating of said sensor element to said host device is facilitated via one or more retention features on said frame and said sensor element.

6. The sensor assembly of claim 1, wherein said frame has a substantially smaller surface area on a radial side than on an ulnar side when disposed on said subject.

7. The sensor assembly of claim 1, wherein said frame further comprises a substantially compliant foam backing having at least one adhesive surface adapted to adhere to tissue of said subject.

8. The sensor assembly of claim 1, wherein said assembly comprises an apparatus adapted to facilitate alignment of said sensor element above an artery of said subject without use of an external alignment apparatus.

9. A method of sensing one or more hemodynamic parameters of a living subject, said method comprising:
    disposing at least one sensor element on said subject, said sensor element being encircled by a suspension loop which is coupled to a substantially conformal frame via at least one flexible suspending arm extending therefrom;
    mating said sensor element to a host device, said mating further comprising mating of an electrical interface of said sensor element to a corresponding electrical interface of said host device;
    using said host device to automatically position said sensor element at a prescribed monitoring location, and calibrate said sensor element; and
    measuring said one or more parameters of said subject using said calibrated sensor element;
    wherein said mating of said host device with said sensor element comprises simultaneously forming both electrical and mechanical connections.

10. The method of claim 9, further comprising automatically zeroing said sensor element.

11. The method of claim 10, wherein said automatic zeroing comprises at least one of:
    checking for a quiescent state comprising a substantially steady sensor electrical output; and
    retracting said sensor away from tissue of said living subject, and performing one or more sample applanation functions.

12. The method of claim 9, further comprising:
    decoupling said host device from said sensor element;
    re-mating said host device and said sensor element after a period of time; and
    obtaining second measurements of said one or more parameters of said subject without having to recalibrate said sensor element.

13. The method of claim 9, further comprising evaluating whether proper mechanical and electrical coupling has been achieved by evaluating a presence of an electrical attribute associated with said sensor element.

14. The method of claim 13, wherein said attribute comprises at least one of:
    determining whether electrical continuity between said sensor element and said host device exists; or
    attempting to access a storage device on said sensor element using circuitry in said host device.

15. A sensor assembly adapted to sense a hemodynamic parameter from a living subject, comprising:
    a frame configured to substantially conform to an anatomy of said living subject when applied thereto;
    a flexible suspension apparatus, said suspension apparatus comprising a loop feature and at least one suspending arm configured to extend therefrom and attach to said frame; and
    a sensor element, said sensor element coupled to said frame via said flexible suspension apparatus such that an entirety of said sensor element is encircled by said loop feature thereof and held to said frame via said at least one suspending arm, said sensor element further comprising a plurality of electrical conductors exposed on at least one surface thereof;
    wherein said plurality of electrical conductors are disposed on said surface of said sensor element so as to enable said sensor element to form an electrical connection with a corresponding electrical interface of a host device during mating of said sensor element to said host device.

16. The sensor assembly of claim 15, wherein said sensor element further comprises:
    a biasing element;
    a pressure transducer; and
    a housing element adapted to encase at least a portion of said sensor element.

17. The sensor assembly of claim 16, wherein said housing element comprises a substantially pyramid-shaped portion, at least a portion of said electrical conductors being disposed thereon.

18. The sensor assembly of claim 15, wherein said host device comprises an actuator.

19. The sensor assembly of claim 15, wherein said mating of said sensor element to said host device is facilitated via one or more retention features on said frame and said sensor element.

20. The sensor assembly of claim 15, wherein said assembly further comprises an apparatus configured to facilitate alignment of said sensor element above an artery of said subject without use of an external alignment apparatus.

* * * * *